(12) United States Patent
Schon et al.

(10) Patent No.: US 8,887,746 B2
(45) Date of Patent: Nov. 18, 2014

(54) ELECTRONIC AND MANUAL BACKUP FLOW CONTROL SYSTEMS

(71) Applicant: Mindray DS USA, Inc., Mahwah, NJ (US)

(72) Inventors: Peter B. Schon, New York, NY (US); Richard G. Cipolli, Nanuet, NY (US); Geoffrey C. Jawidzik, Mahwah, NJ (US); Luo Jiancheng, Shenzhen (CN); Li An, Shenzhen (CN); Hu Min, Shenzhen (CN)

(73) Assignee: Mindray DS USA, Inc., Mahwah, NJ (US)

( * ) Notice: Subject to any disclaimer, the term of this patent is extended or adjusted under 35 U.S.C. 154(b) by 261 days.

(21) Appl. No.: 13/677,122

(22) Filed: Nov. 14, 2012

(65) Prior Publication Data

US 2014/0130880 A1    May 15, 2014

(51) Int. Cl.
| | | |
|---|---|---|
| *F17D 1/02* | (2006.01) | |
| *F17D 3/12* | (2006.01) | |
| *F16K 31/06* | (2006.01) | |
| *A61M 16/00* | (2006.01) | |
| *A61M 21/00* | (2006.01) | |

(52) U.S. Cl.
CPC ....... *A61M 16/00* (2013.01); *A61M 2021/0066* (2013.01)
USPC ........ 137/1; 137/601.14; 251/96; 251/129.11

(58) Field of Classification Search
USPC ............. 137/1, 601.14, 607, 597; 251/95, 96, 251/129.01, 129.03, 129.04, 129.11
See application file for complete search history.

(56) References Cited

U.S. PATENT DOCUMENTS

| | | | | |
|---|---|---|---|---|
| 5,095,941 | A * | 3/1992 | Betz | 137/552 |
| 5,511,763 | A * | 4/1996 | Green | 251/129.02 |
| 5,595,216 | A * | 1/1997 | Pilolla | 137/607 |
| 6,024,087 | A | 2/2000 | Kersey et al. | |
| 6,481,634 | B1 * | 11/2002 | Zosimadis | 236/12.12 |
| 7,066,192 | B1 * | 6/2006 | Delaney et al. | 137/15.18 |
| 7,150,293 | B2 * | 12/2006 | Jonte | 137/613 |
| 7,624,757 | B2 * | 12/2009 | Schmitt | 137/606 |
| 7,946,504 | B2 * | 5/2011 | Shapira et al. | 236/12.12 |
| 8,561,626 | B2 * | 10/2013 | Sawaski et al. | 137/1 |
| 2009/0261282 | A1 * | 10/2009 | Connors | 251/129.01 |
| 2012/0032100 | A1 * | 2/2012 | Kim et al. | 251/129.03 |

* cited by examiner

*Primary Examiner* — Stephen M Hepperle
*Assistant Examiner* — Seth W Mackay-Smith
(74) *Attorney, Agent, or Firm* — Kory D. Christensen; Stoel Rives LLP

(57) ABSTRACT

In various embodiments, an electronic flow selector of a fluid flow control system may be used to select a flow rate of a fluid. When the system is in an electronic mode, an encoder may electronically encode the fluid flow selection. A controller may receive the electronically encoded flow selection and transmit a corresponding control signal to an electronic valve to allow the fluid to flow at the selected flow rate. When the system is in a manual mode, backup manual flow selectors may be used to directly control the flow rate of a fluid. When the system is in a manual mode, the mechanical backup flow selectors may be in a deployed position. When the system is in an electronic mode, the mechanical backup flow selectors may be in a retracted position. Particular applications to gases and anesthesia delivery are disclosed herein.

28 Claims, 18 Drawing Sheets

ELECTRONIC AND MANUAL BACKUP FLOW CONTROL SYSTEMS

TECHNICAL FIELD

This disclosure relates generally to controlling the flow of fluids via manually adjustable controls. Particularly, this disclosure relates to a mechanical backup flow control system for use with an electronic flow control system.

SUMMARY

In various instances, the rates of flow of fresh gases, such as oxygen, nitrous oxide, and air, in modern anesthesia delivery systems may be controlled by a practitioner either electronically or mechanically. In various embodiments, one or more flow selectors (e.g., rotatable knobs) may be configured to electronically select a flow rate of a gas when in an electronic mode. The anesthesia delivery system may also include manual backup controls for controlling the flow rate of one or more of the gases when in an unpowered state. In one embodiment, three-way selector valve and/or a combination of normally-open valves and normally-closed valves may be used to selectively enable the flow of gas from either electronically controlled electronic proportional valves or mechanically operated needle valves.

For instance, when a fluid flow control system is in an electronic mode, a three-way selector valve, or other diversion valve system, may allow fluid from the electronically controlled electronic proportional valves to be delivered to a patient. When the fluid flow control system is in an unpowered state or a manual override is selected, the three-way selector valve may allow fluid from the mechanically controlled needle valves to be delivered to a patient. Alternatively, a diversion valve system may include a combination of normally-open and normally-closed valves instead of or in addition to a three-way selector valve, as described herein. In some embodiments, the diversion valve system may be located between a fluid supply and a fluid control valve. In other embodiments, the diversion valve system may be located between a fluid control valve and a fluid output.

An electronic flow control valve may be configured to selectively receive a fluid from a fluid supply. An electronic flow selector may allow a practitioner to select a flow rate of the first fluid via the electronic flow control valve. For example, an encoder may electronically encode a selection made via the electronic flow selector and transmit the encoded selection to an electronic controller. The electronic controller may transmit a control signal to the electronic flow control valve to control the flow rate of the fluid based on the selection made via the electronic flow selector. The electronic flow control valve may include an electronic proportional valve and the electronic flow selector may include a rotary knob configured to be manually rotated by a practitioner. Alternatively, the electronic flow selector may include any of a wide variety of digital and/or analog selectors.

In some embodiments, a unique electronic flow control valve may be used to control the flow rate of each available fluid. A unique electronic flow selector may be available to control the flow rate of each of the electronic flow control valves. Alternatively, one or more of the electronic flow selectors may be selectively assignable to control two or more electronic flow control valves. For example, a system may include three electronic flow control valves, one for oxygen, one for air, and one for nitrous oxide. The system may incorporate only two electronic flow selectors, one of which may be selectively used to control either the flow rate of the air or the flow rate of the nitrous oxide. Any electronic flow selector may be permanently assigned or selectively assigned to control the flow rate of any one or more of the available fluids.

One or more mechanical flow control valves may be configured to control the flow rate of each of the available fluids. For example, a unique needle valve may be used to mechanically control the flow rate of each available fluid. A manual flow selector, such as a knob or slider, may be actuated by a practitioner to mechanically adjust the flow rate through each of the needle valves. In some embodiments, the manual flow selectors may be disabled and/or retracted to prevent adjustments when the system is in an electronic mode.

Accordingly, in an electronic mode, one or more electronic flow selectors may be adjusted to control the flow rate of one or more fluids through one or more electronic flow control valves. In the powered state, backup mechanical flow control valves may be disabled and/or otherwise prevented from supplying a fluid or combination of fluids. Moreover, in the powered state, manual flow selectors associated with the backup mechanical flow control valves may be disabled and/or retracted to prevent adjustments.

In an unpowered state, or when a manual override selection is made, the electronic flow control valves may be disabled and/or otherwise prevented from supplying a fluid or combination of fluids. Manual flow selectors may be enabled and/or deployed to allow a practitioner to manually control a flow rate of one or more fluids through the backup mechanical flow control valves.

In some embodiments, when the manual flow selectors are retracted, such as upon power restoration or a reset of the system, the flow rate of each of the backup mechanical flow control valves may be reset to a home state, in which a predetermined flow rate of a gas will automatically flow when the system enters an unpowered state.

In one embodiment, the electronic flow control valve may comprise an electronically controlled stepper motor configured to adjust the flow rate of a fluid through a mechanical flow control valve, such as a needle valve. In various examples provided herein, the fluid is described as a gas, such as oxygen, nitrous oxide, and/or air. However, any of a wide variety of liquids and/or gases may be used in conjunction with various embodiments of the systems and methods described herein.

DETAILED DESCRIPTION

Figure 1:
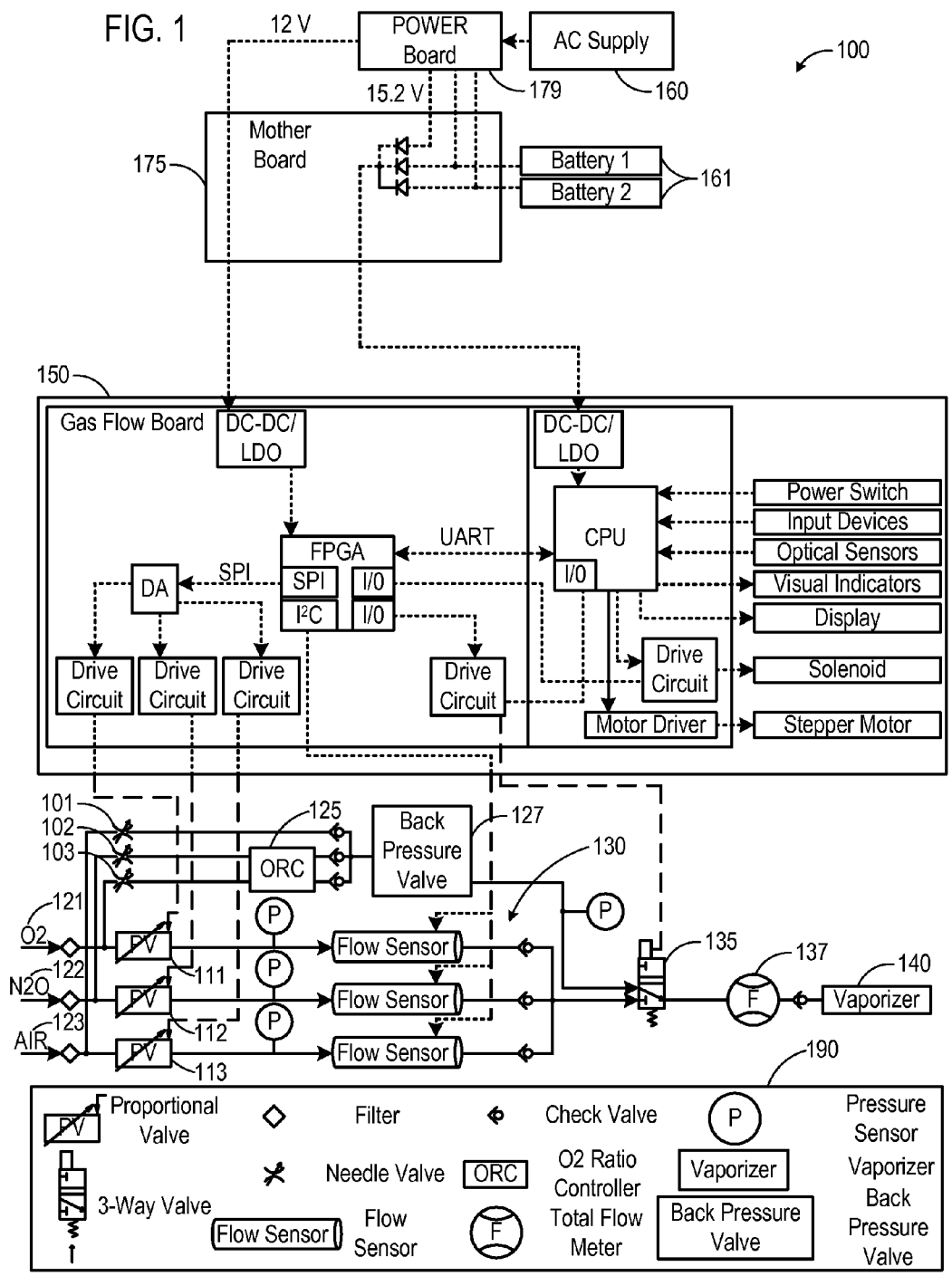
FIG. 1 illustrates a diagram of an anesthesia delivery system configured with electronic and backup manual controls for controlling the flow of oxygen, nitrous oxide, and air.

While electronic flow control of gases may be useful during anesthesia delivery, it may be desirable to provide manual backup controls as well. For example, in the event of power loss, it may be desirable to continue supplying gases during anesthesia delivery. In some embodiments, electronic controls, such as trim knobs, used in conjunction with encoders, may facilitate the electronic adjustment of the flow rate of one or more gases during anesthesia delivery. Separate backup knobs may be available for use in the event of power failure or power unavailability. In such embodiments, the practitioner may need to engage the backup knobs, switch the machine from an electronic mode to a manual mode, and/or ensure that the manual knobs are set to a desirable state prior to switching to a manual mode.

Power loss during anesthesia delivery may be confusing and/or disruptive during a critical medical procedure. It may be an inconvenience and/or confusing for a practitioner to see two sets of knobs for controlling the same set of gases. In various embodiments of the present disclosure, flow selectors, such as rotary knobs, may be electronically operable when a fluid flow control system is in an electronic mode and backup flow selectors may be retracted or otherwise disabled when a fluid flow control system is in an electronic mode. In an unpowered state, or when a practitioner engages the backup system, the backup flow selectors may be deployed or otherwise enabled.

The number of diversion valve systems, mechanically operated valves, electronically operated valves, controllers, encoders, flow selectors, and/or other components described herein may correspond to the number of gases (or liquids) available. In various anesthesia delivery systems, oxygen, nitrous oxide, and/or air may each be independently controllable and/or proportionally controllable. A mixture of one or more gases may be used in conjunction with a vaporizer to deliver anesthesia.

In one embodiment, a diversion valve system may direct the flow of a gas (or liquid) from a gas supply to either a mechanical flow control valve, such as a mechanically operated needle valve, or an electronic flow control valve, such as an electronic proportion valve, depending on whether or not the system has power or if a backup system has been engaged.

If the system is in an electronic mode, the selected flow rate may be encoded and transmitted to a controller. The controller may then send a control signal to the electronic proportion valve in order to achieve the selected flow rate. A deployment assembly may maintain the backup flow control valves in a retracted state. Alternatively, a deployment assembly may maintain the backup flow control valves in a disabled or non-functioning state.

If the system is in an unpowered state or a backup system is engaged by a practitioner, the backup flow selectors may be deployed, enabled, and/or otherwise caused to function. A selected flow rate may then be mechanically translated from a manual flow selector to a mechanically operated flow control valve, such as a needle valve, to achieve the selected flow rate.

According to various embodiments, the diversion valve system may include normally-open and normally-closed valves in order to selectively prevent the gas from flowing from (or to) both the mechanically operated needle valve and the electronic proportion valve. The diversion valve system may be implemented using any of a wide variety of valves and/or control systems, such as a three-way selector valve.

In some embodiments, the needle valve may be used as the mechanical flow control valve and the same needle valve in combination with the electronic stepper motor may be considered the electronic flow control valve. In various embodiments, the flow selector may comprise any of a wide variety of knobs, buttons, rotatable actuators, slides, and/or other analog and/or digital selection devices. In various embodiments, a controller or control system may be implemented as any combination of hardware, firmware, and/or software. For example, a controller may be implemented as a field-programmable gate array (FPGA). In some embodiments, an electronic controller for transmitting a control signal to an electronic flow control valve may be distinct from other electronic components in a gas flow control system, such as microprocessors and other electronic components associated with displays, touch screens, data storage, data connectivity, etc. The reliability of the electronic flow controls may be improved by separating the electronic flow controls from other electronic features of an anesthesia delivery device and/or by implementing it in hardware rather than software.

While the various examples and embodiments disclosed herein are described in conjunction with a gas flow control system, many of the embodiments could be used or modified for use with any type of fluid, including various gases and liquids. Gases used for anesthesia delivery, such as oxygen, nitrous oxide, and air, are used herein as examples of gases that can be controlled via the presently described fluid flow control systems and are referred to as gas flow control systems.

Some of the infrastructure that can be used with embodiments disclosed herein is already available, such as general-purpose computers, computer programming tools and techniques, digital storage media, and communication networks. A computing device or other electronic controller may include a processor, such as a microprocessor, a microcontroller, logic circuitry, and/or the like. The processor may include a special purpose processing device such as application-specific integrated circuits (ASIC), programmable array logic (PAL), programmable logic array (PLA), a programmable logic device (PLD), FPGA, or another customizable and/or programmable device. The computing device may also include a machine-readable storage device, such as non-volatile memory, static RAM, dynamic RAM, ROM, CD-ROM, disk, tape, magnetic, optical, flash memory, or other machine-readable storage medium. Various aspects of certain embodiments may be implemented using hardware, software, firmware, or a combination thereof.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once.

FIG. 1 illustrates a diagram 100 of an anesthesia delivery system configured with electronic flow control valves 111, 112, and 113 and backup mechanical flow control valves 101, 102, and 103 for controlling the flow of oxygen 121, nitrous oxide 122, and air 123. When power is available via AC supply 160 and/or batteries 161, the anesthesia delivery system may utilize electronic flow control valves 101, 102, and 103 controlled by one or more electronic flow selectors. The power input may be converted and/or inverted as necessary by a power board 179 and/or motherboard 175. A gas flow board 150 may include various monitoring and/or control components for electronically monitoring, regulating, and/or controlling the flow of gases within the anesthesia delivery system.

In various embodiments, the anesthesia delivery system may include various components and/or interface with various components via the gas flow board 150. For example, the gas flow board 150 may include and/or communicate with various FPGA's, CPUs, microprocessors, logic circuits, drive circuits, digital to analog converters, analog to digital converters, drive circuits, motor drivers, power switches, input devices, optical sensors, visual indicators, displays, solenoids, stepper motors, touch panels, and/or peripheral devices. Additionally, the gas flow board 150 may include and/or communicate with position switches, LED, needle valve switches, gas source, and/or other selection inputs. A practitioner may interact with the anesthesia delivery machine by providing inputs with regards to a flow of one or more gases. For instance, a practitioner may provide an input via an electronic flow selector. The electronic flow selector may comprise a mechanically rotatable knob and a rotary encoder.

When the anesthesia delivery system is in an electronic mode, the user may utilize an electronic mode or select a manual mode. When the anesthesia delivery system is in an unpowered state, the anesthesia delivery system may be used in a manual mode. In the electronic mode, the three source gases, oxygen 121, nitrous oxide, 122, and air 123, may flow through the electronic flow control valves 111, 112, and 113, an oxygen ratio controller 125, and/or check valves 130 and flow sensors. In a manual mode, the three source gases 121, 122, and 123 may flow through backup mechanical flow control valves 101, 102, and 103, oxygen ratio controller 125, and/or backpressure valve 127.

In various embodiments, a user may achieve a desired ratio of gases 121, 122, and 123 by starting with zero flow and sequentially adding source gases to the total flow, noting the effect of each on total flow rate. In an alternative embodiment, the user may achieve a desired ratio of gases 121, 122, and 123 by starting at a "home state" flow of oxygen 121 and then adjust each of the gases 121, 122, and 123 to achieve the desired flow rate. The oxygen ratio controller 125 may ensure a clinically safe ratio of oxygen to nitrous oxide and/or oxygen to air. The check valves 130 may prevent back flow of gases 121, 122, and 123 due to potential higher downstream pressures.

According to various embodiments, a user may select a flow rate of a combination of oxygen and air to be supplied to a patient. A user may also select a flow rate of nitrous oxide to be provided to a patient instead of air. In some embodiments, the nitrous oxide may be supplied in addition to air. Regardless of the selections made by a user, a safe amount of oxygen may be automatically supplied to the patient, as ensured by the oxygen ratio controller (ORC) 125.

In either flow control mode, after passing through the check valves 130, the flows of the three gases 121, 122, and 123 may be combined into a single flow, which may be measured by a total flow meter, and pass through a total flow meter 137. An anesthetic gas vaporizer 140 may vaporize an anesthetic into the gases. A three-way selector valve 135 may be used to direct a flow of gases from only one of the backup mechanical flow control valves 101, 102, and 103 and the electronic flow control valves 111, 112, and 113. Alternatively, the three-way selector valve may comprise a one or more normally-open and/or normally-closed valves. Alternative diversion valve systems may be employed in place of a three-way selector valve 135 and/or normally-open and/or normally-closed valves.

In an electronic mode, flow control selectors associated with the backup mechanical flow control valves 101, 102, and 103 may be disabled, retracted, locked, and/or otherwise disengaged. In a manual mode (whether entered due to power loss or user selection), flow control selectors associated with the needle valves 101, 102, and 103 may be enabled, deployed, unlocked, and/or otherwise engaged. Various elements of the diagram 100 are illustrated in the key 190 and are not described in detail herein. Additionally, any of a wide variety of components, measurement devices, monitoring devices, and/or control devices configured for use in anesthesia delivery systems, gas delivery systems, liquid delivery systems, and/or other related systems may be added to, supplemented within, and/or replace components within the illustrated system.

Figure 2A:
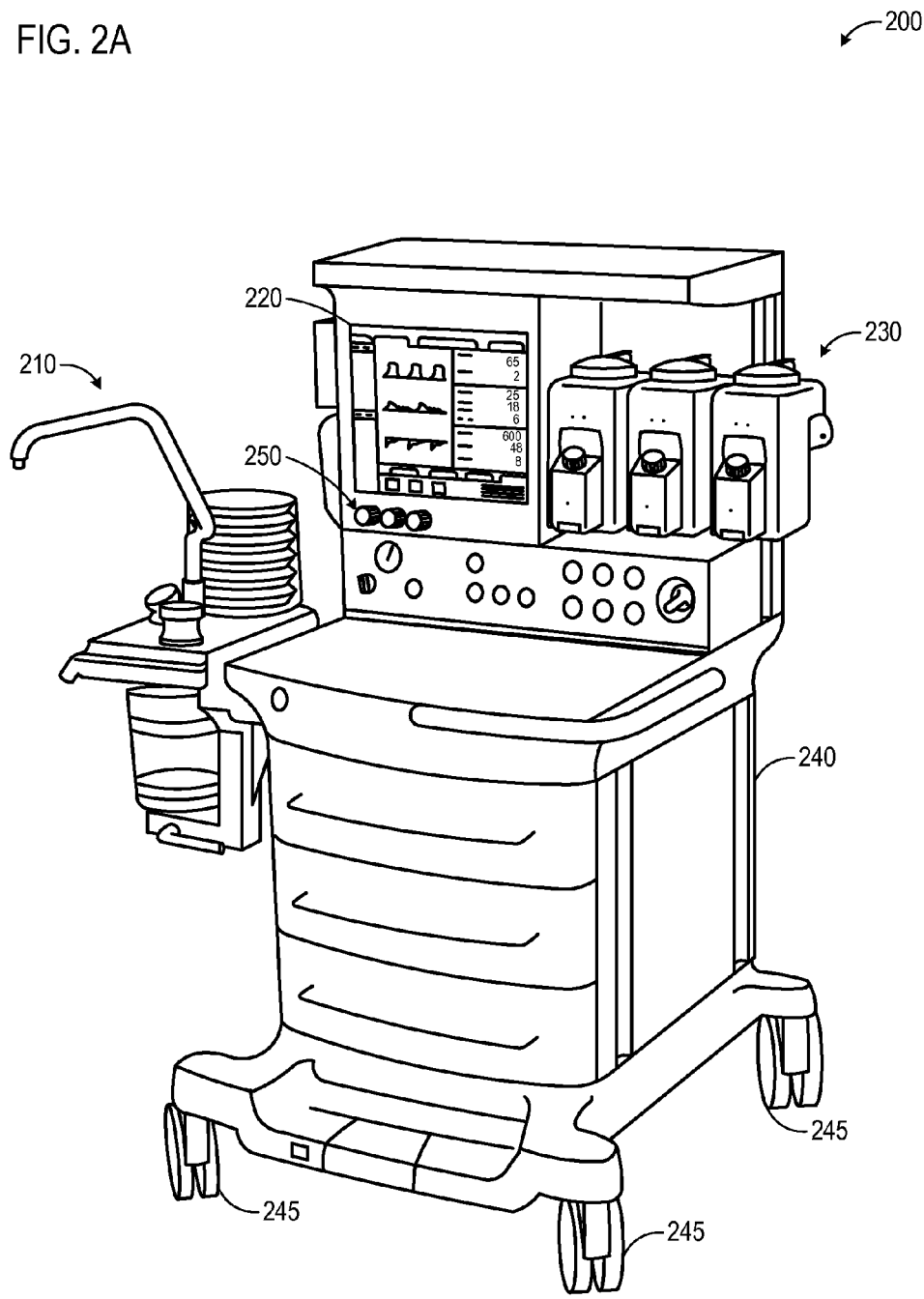
FIG. 2A illustrates an anesthesia delivery machine configured with three manual flow selectors, one each for controlling the flow of oxygen, nitrous oxide, and air.

FIG. 2A illustrates an anesthesia delivery machine 200 configured with three manual flow selectors 250, one each for controlling the flow of oxygen, nitrous oxide, and air. The illustrated anesthesia delivery machine 200 may include a breathing system 210, anesthetic gas vaporizers 230, and/or other components of an anesthetic delivery system. The anesthesia delivery machine 200 may include a cart 240 and/or wheels 245 for portability. An electronic display 220 may provide information regarding the flow rate and/or anesthetic delivery process to a practitioner. Additionally, the electronic display 220 may be configured as a touch sensitive display to allow a practitioner to provide a selection of a flow rate.

Figure 2B:
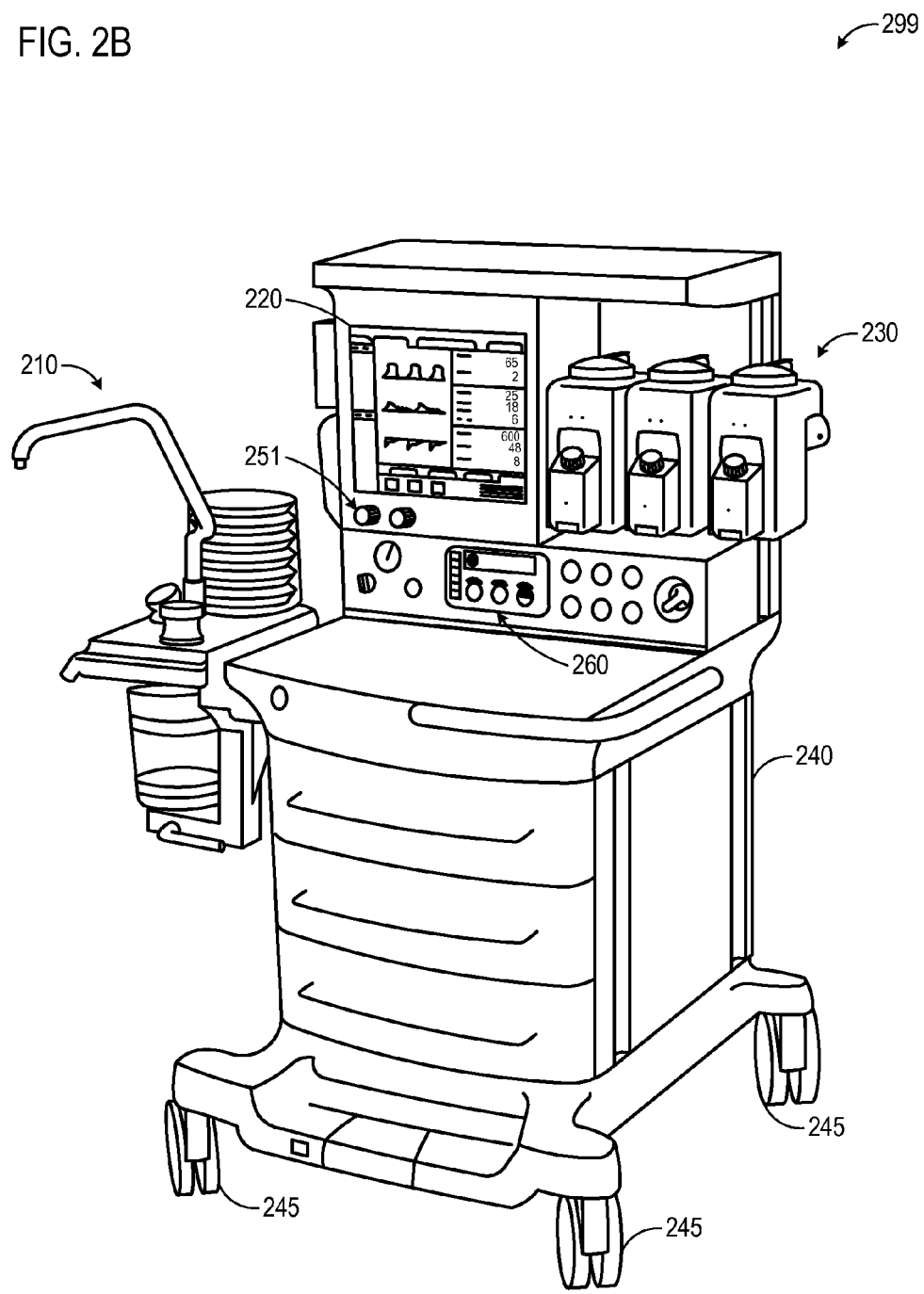
FIG. 2B illustrates an anesthesia delivery machine configured with two electronic flow control selectors, configurable to selectively control each of the three gases, and three backup manual flow selectors, for controlling each of the three gases.

FIG. 2B illustrates an anesthesia delivery machine 299 configured with two electronic flow control selectors 251, configurable to select a flow rate for each of the three gases, and three backup manual flow selectors 260, for controlling each of the three gases. Similar to the embodiment illustrated in FIG. 2A, the anesthesia delivery machine 299 may include a breathing system 210, anesthetic gas vaporizers 230, and/or other components of an anesthetic delivery system. The anesthesia delivery machine 299 may include a cart 240 and/or wheels 245 for portability. An electronic display 220 may provide information regarding the flow rate and/or anesthetic delivery process to a practitioner. Additionally, the electronic display 220 may be configured as a touch sensitive display to allow a practitioner to provide a selection of a flow rate.

The three backup manual flow selectors 260 may remain retracted and/or disabled when the anesthesia delivery machine 299 is in an electronic mode. When the anesthesia delivery machine 299 enters a manual mode (e.g., due to power loss or a user selection), the three backup manual flow selectors 260 may be deployed, unlocked, and/or otherwise function. As previously described, various internals, switches, normally-open valves, normally-closed valves, three-way valves, and/or other components may regulate the flow of gases within the anesthesia delivery machine 299 based on whether it is in a manual mode or an electronic mode.

Figure 3:
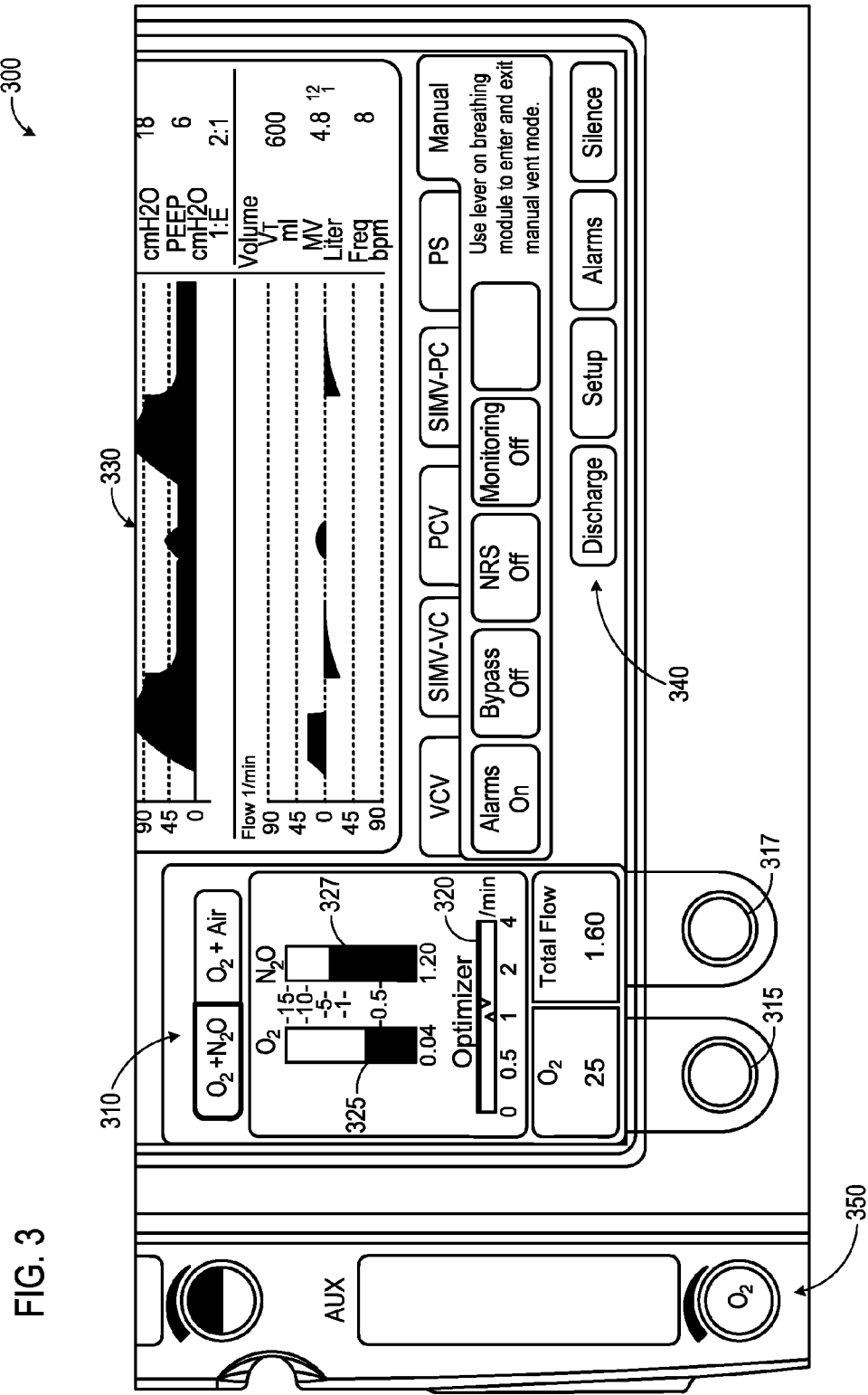
FIG. 3 illustrates a close-up view of a control panel of an anesthesia delivery machine, including two electronic flow control selectors selectively configurable to control either oxygen and nitrous oxide, or oxygen and air.

FIG. 3 illustrates a close-up view of a control panel 300 of an anesthesia delivery machine, including two electronic flow control selectors 315 and 317 selectively configurable to control either oxygen and nitrous oxide, or oxygen and air. As illustrated, the anesthesia delivery machine may include a panel 330 to display various telemetry data associated with a patient, information associated with the flow rate of gases, and/or information associated with the delivery of one or more anesthetics. Various inputs 340 may be available to change the display of panel 330 and/or to control the anesthesia delivery machine.

In a first position, a selection toggle 310 may allow a practitioner to control the flow rate of oxygen and nitrous oxide via the respective electronic flow control selectors 315 and 317. In a second position, the selection toggle 310 may allow a practitioner to control the flow rate of oxygen and air via the respective flow control selectors 315 and 317. Depending on the position of the selection toggle 310, various flow rate monitoring devices and ratio measuring devices 320, 325 and 327 may indicate the flow rate of one or more gases and/or combination of gases. In various embodiments, auxiliary inputs and outputs 350 for oxygen and/or another gas may be available.

While the illustrated embodiment shows two electronic flow control selectors 315 and 317, any number of flow selectors and associated gases may be utilized. For example, a flow control system may be configured to allow for the electronic and backup manual control of one, two, three, four . . . or N number of gases or liquids. In some embodiments, more than one flow control selector (e.g., knob, toggle, dial, slider, switch) may be configured to control the flow rate of the same gas. Additional selection toggles 310 and/or a multi-position selection toggle, may be used to control the number of gases controlled by any number of corresponding flow control selection knobs. The flow control selectors may include and/or utilize any analog or digital selection mechanism for selecting a flow rate, including knobs as illustrated in the figures.

Figure 4:
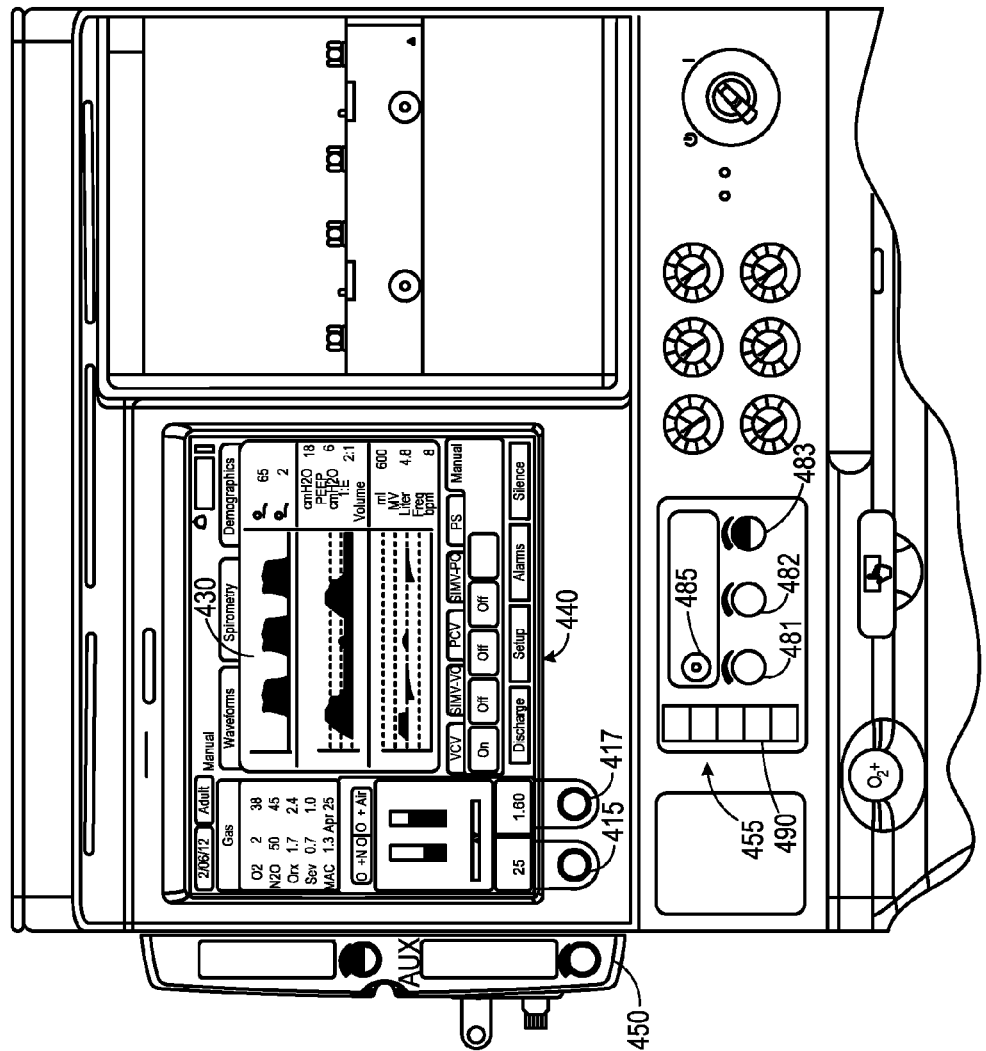
FIG. 4 illustrates a wider view of a control panel of an anesthesia delivery machine, including backup manual flow controls for controlling the flow of three gases independently.

FIG. 4 illustrates a wider view of a control panel 400 of an anesthesia delivery machine, including backup manual flow controls 481, 482, and 483 for controlling the flow of three gases independently. When the anesthesia delivery system is in an electronic mode and the user has not selected a manual mode, the anesthesia delivery system may be in an electronic mode. In an electronic mode, two electronic flow control selectors 415 and 417 may be used to control either oxygen and nitrous oxide or oxygen and air, depending on the selection made via a selection toggle. An electronic display 430 may display information associated with the flow rate of one or more gases, an anesthetic, and/or patient telemetry data. Various touch inputs 440 may be available. An auxiliary control panel 450 may allow for one or more gases to be supplied to an auxiliary device.

When the anesthesia delivery system is in an unpowered state and/or the user has selected a manual mode, the anesthesia delivery system may be in a manual mode. In a manual mode, the flow rate of one or more gases and/or the amount of anesthetic delivery may be controlled via a manual panel 455. The electronic display 430, the touch inputs 440, the electronic flow control selectors 415 and 417, and other electronic components may be unavailable in an unpowered state and one or more of them may be unavailable and/or otherwise disabled in a manual mode selected when in a powered state.

The manual panel 455 may include a total flow rate indicator 490, a manual mode selector 485 (e.g., a spring-loaded plunger), and one or more manually operated flow control selectors 481, 482, and 483. According to various embodiments, a manually operated flow control selector may be available for each available gas or for each available critical gas. In various embodiments, manually operated flow control selectors 481, 482, and 483 may be disabled, retracted, locked, and/or otherwise not operational when the anesthesia delivery system is in an electronic mode. In a manual mode, the manually operated flow control selectors 481, 482, and 483 may be enabled, deployed, unlocked, and/or otherwise become operational.

Figure 5:
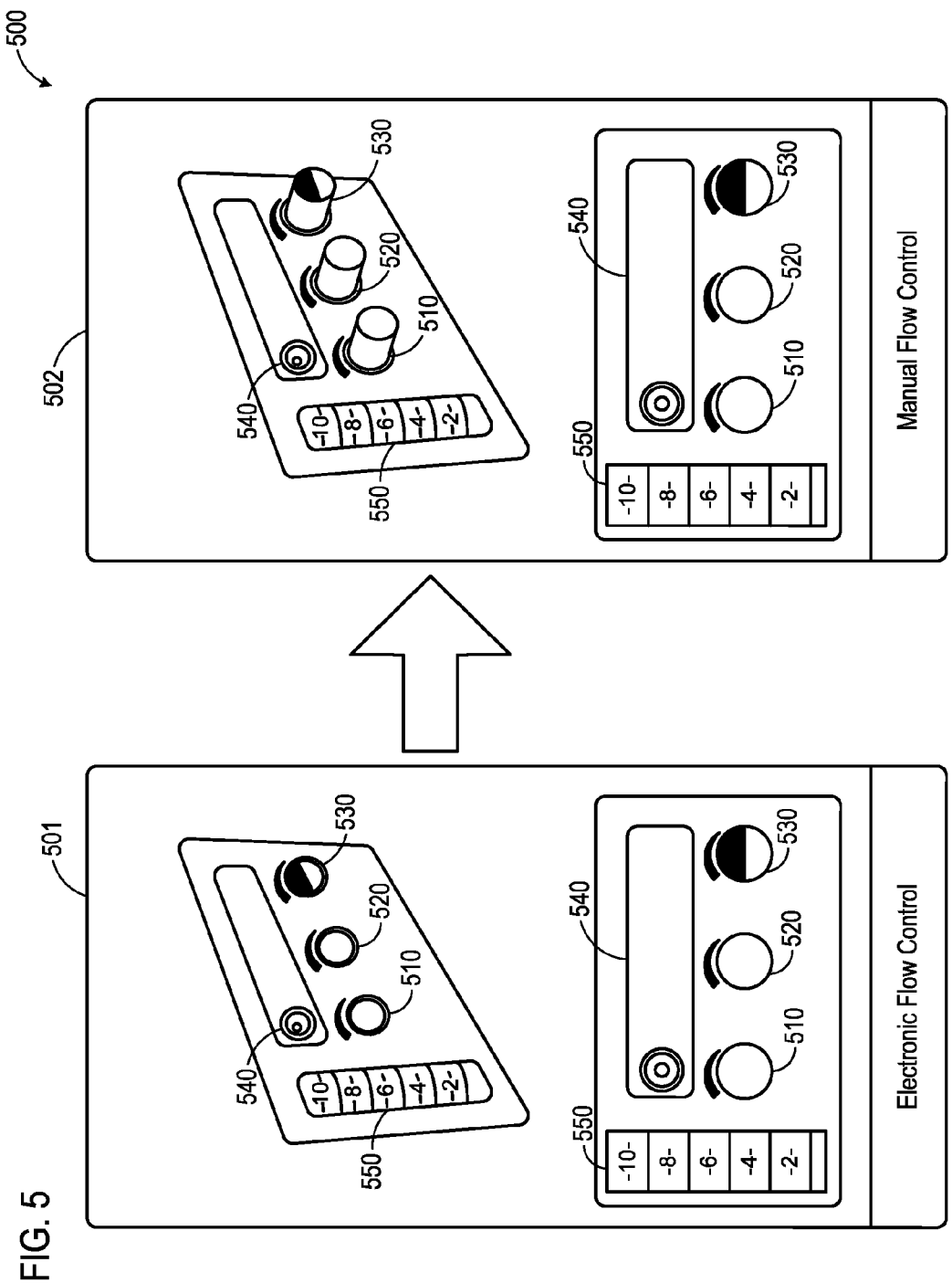
FIG. 5 illustrates an exemplary embodiment of backup manual flow selectors in a retracted state and the backup manual flow selectors in a deployed state.

FIG. 5 illustrates an exemplary embodiment 500 of backup manual flow selectors 510, 520, and 530 in a retracted state 501 and the backup manual flow selectors 510, 520, and 530 in a deployed state 502. The illustrated embodiment includes a perspective view (top of 501 and 502) and a front view (bottom of 501 and 502). As illustrated, a total flow indicator 550 may be available to indicate the flow rate of one or more gases. A manual mode selector 540 may allow a user to cause an anesthesia delivery system to enter a manual mode even when the system is in a powered state. The system may automatically enter a manual mode when the system transitions from a powered state to an unpowered state. In an electronic mode, the flow control selectors 510, 520, and 530 may remain in a retracted state (501), so as to be unobtrusive, disabled, and/or otherwise not inconvenience or confuse a user. In a manual mode, the flow control selectors 510, 520, and 530 may be deployed (502), so as to be more obtrusive, enabled, and/or otherwise alert a user that they may be used to control the flow rate of one or more gases.

In some embodiments, the default position of a manual flow control selector may be above 0 liters per minute. For example, a default position for a manual flow control selector associated with the flow rate of oxygen may have a home state of 2 liters per minute, so as to continue providing a critical gas to a patient even in the event the anesthesia delivery system loses power during use.

Figure 6:
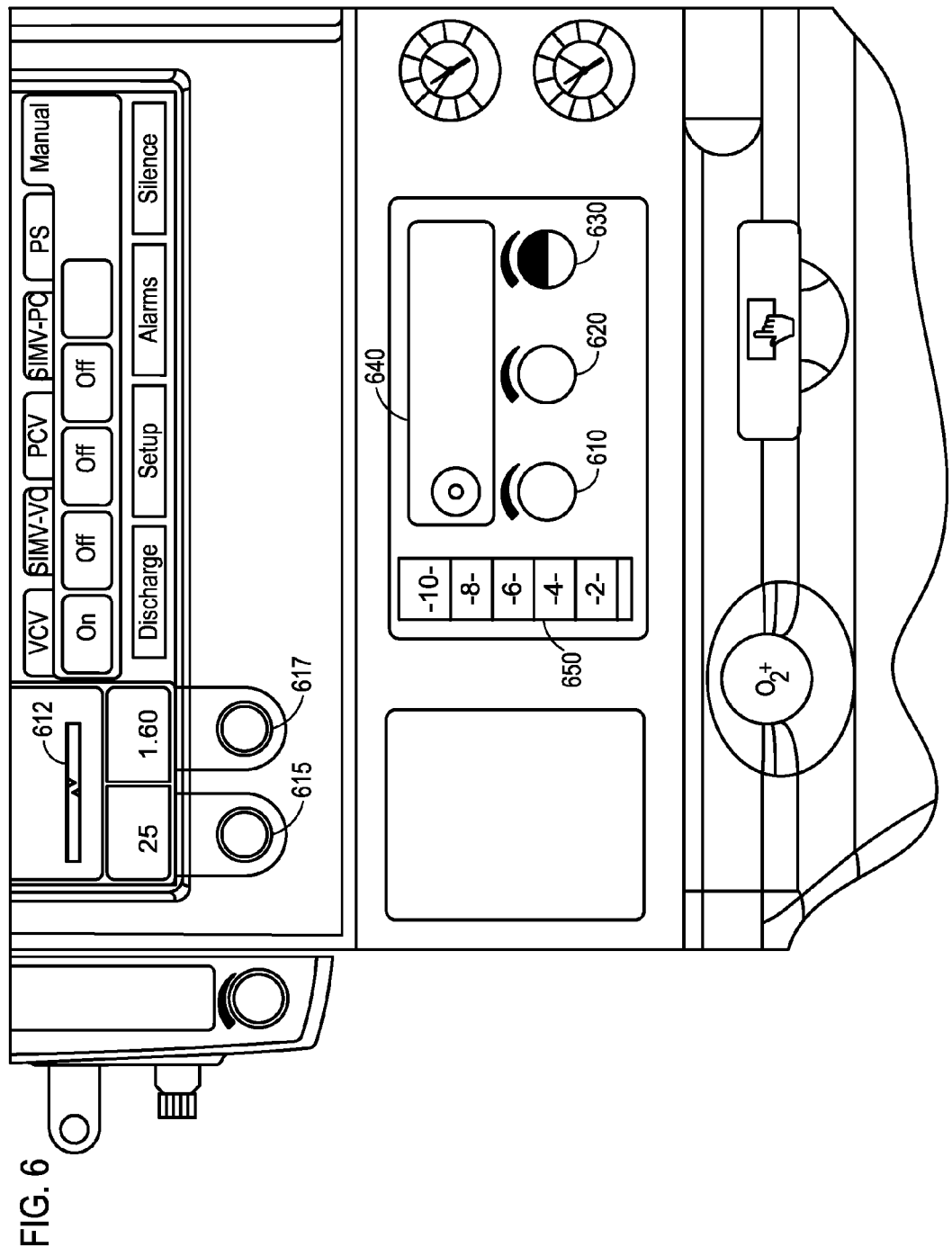
FIG. 6 illustrates another view of a control panel of an anesthesia delivery machine, including both electronic flow control selectors and backup manual flow selectors.

FIG. 6 illustrates another view of a control panel of an anesthesia delivery machine that includes both electronic flow control selectors 615 and 617 and backup manual flow selectors 610, 620, and 630. In an electronic mode, backup manual flow selectors 610, 620, and 630 may be retracted, locked, disengaged, and/or otherwise non-operational. The flow rate of two or more gases may be controlled by the electronic flow control selectors 615 and 617. An optimizer indicator 612 may indicate a total flow rate of gases selected by the electronic flow control selectors 615 and 617.

The anesthesia delivery system may enter a manual mode due to the loss of power and/or in response to a user selecting a manual mode selector 640. In one embodiment, the manual mode selector 640 may include a plunger configured to actuate a solenoid or motor to deploy the manual flow selectors 610, 620, and 630. In a manual mode, a flow rate indicator 650 may indicate the total flow rate of gases as selected by the backup manual flow selectors 610, 620, and 630.

Figure 7:
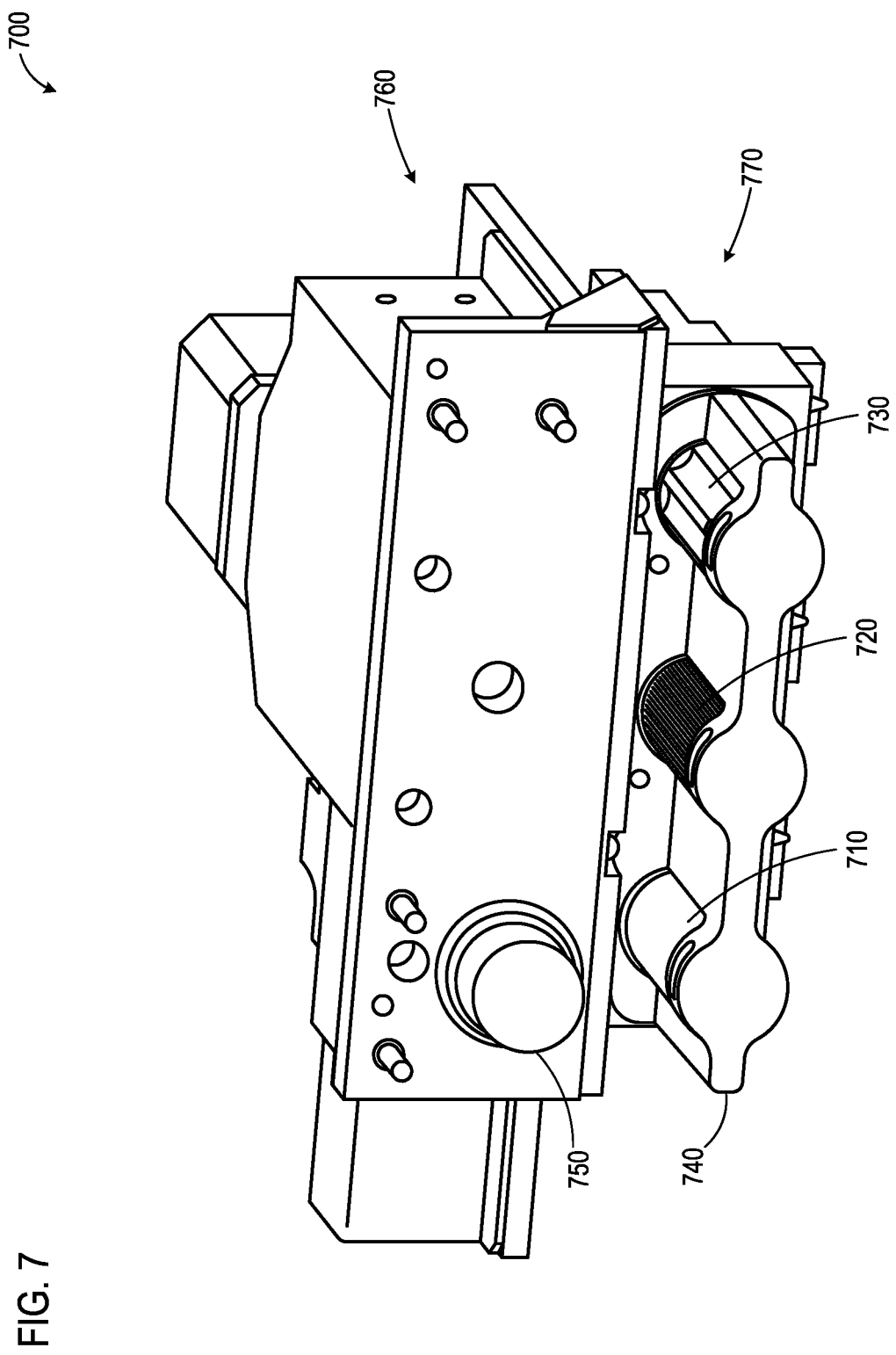
FIG. 7 illustrates a mechanical apparatus configured to selectively deploy and retract three manual flow selectors.

FIG. 7 illustrates a mechanical apparatus 700 configured to selectively deploy and retract three manual flow selectors 710, 720, and 730. According to various embodiments, the mechanical apparatus 700 may be mounted within a housing of an anesthesia delivery system and/or other fluid flow control system. The embodiments of the mechanical apparatus 700 and related embodiments are described herein in conjunction with an anesthesia delivery system and/or other fluid flow control system. However, the mechanical apparatus 700 could be utilized in conjunction with any system or apparatus in which it may be useful to have buttons, knobs, or other selectors selectively deployed and retracted in response to user selection and/or power availability.

As illustrated, a deployment assembly 760 may be mated with a flow selector assembly 770. The flow selector assembly may include one or more (illustrated as three) manual flow selectors 710, 720, and 730. A knob guard 740 may prevent the manual flow selectors 710, 720, and 730 from being actuated when in a retracted state. The deployment assembly 760 may be configured to selectively deploy the flow selector assembly 770 by translating the flow selector assembly 770 from a retracted position to a deployed position. A manual mode selector 750 may be used to manually select a deployed position. Additionally, the deployment assembly 760 may be configured to deploy the flow selector assembly 770 in response to a power disruption.

Figure 8:
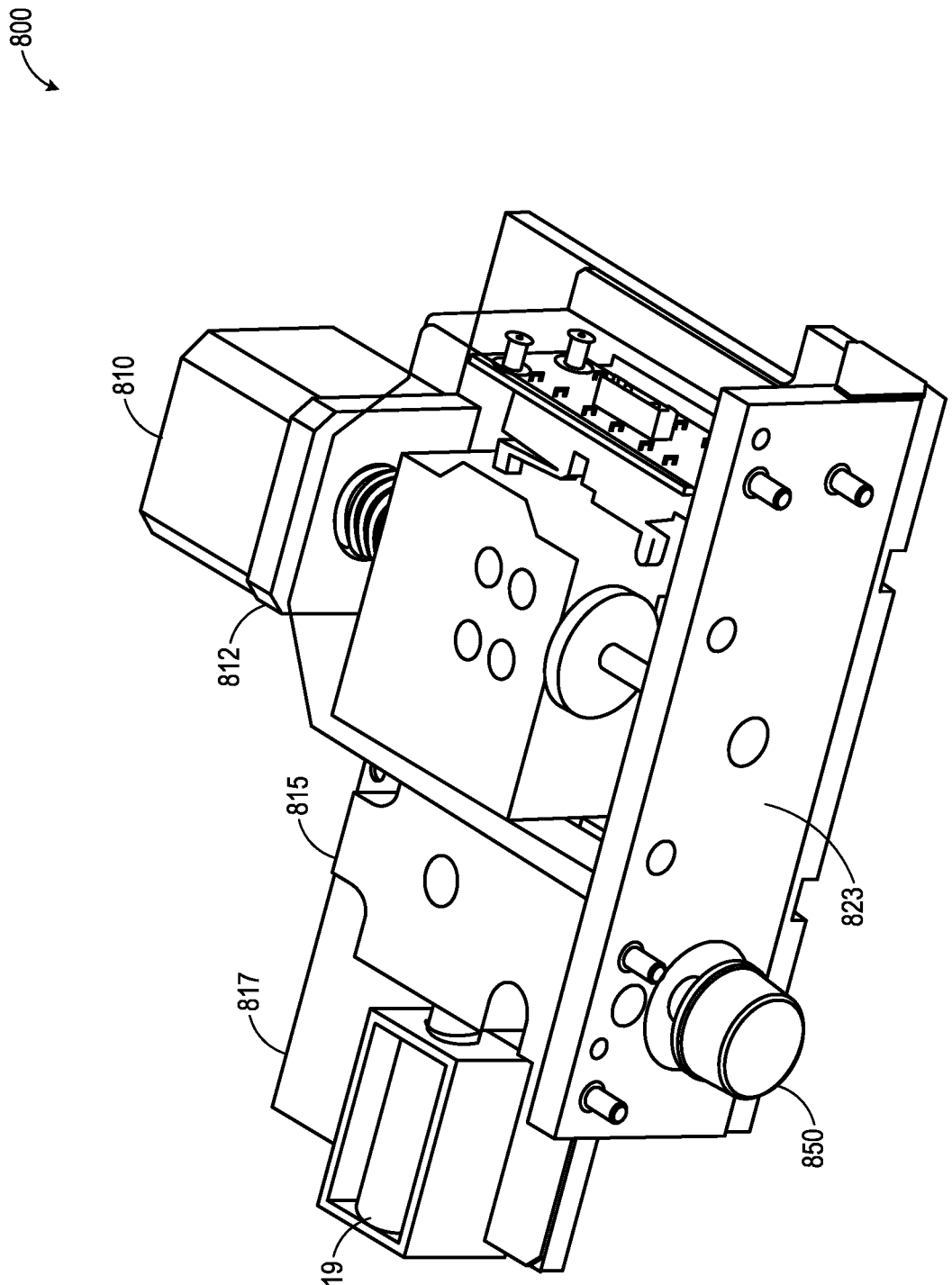
FIG. 8 illustrates a deployment assembly configured to selectively deploy the manual flow selectors.

FIG. 8 illustrates a deployment assembly 800 configured to selectively deploy a flow selector assembly (not shown). The deployment assembly 800 may include a front support plate 823 configured to fasten the mechanical apparatus to an anesthesia machine (or other device). A latch support block 815 and a solenoid 819 may be mounted to a bottom support plate 817. A motor 810 may be mounted to the bottom support plate 817 via a motor mount 812. A button plunger (a manual mode selector) 850 may be mounted to the front support plate 823 and operable to engage components within the latch support block to disengage a latch connected to the solenoid, as described in detail below.

Figure 9:
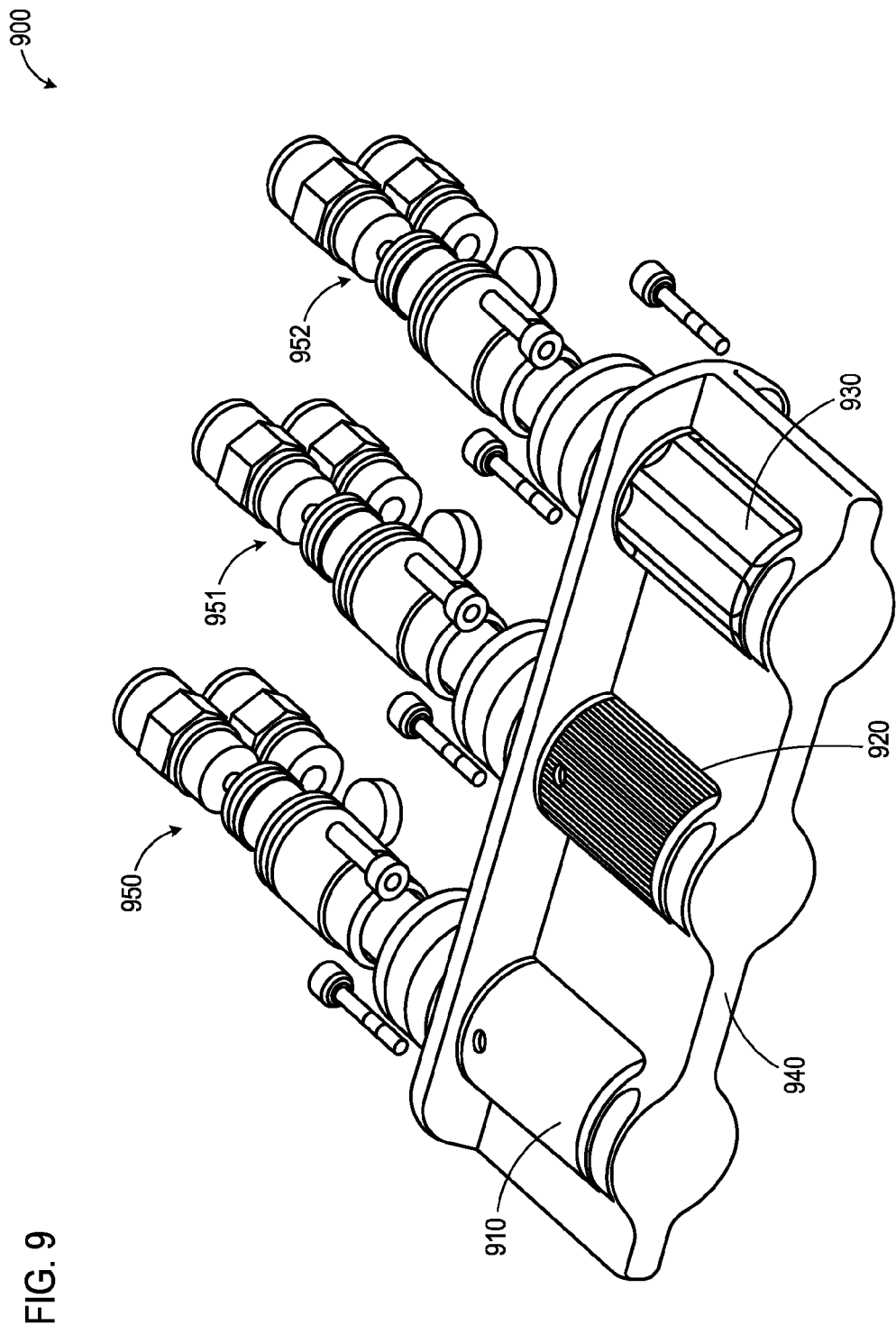
FIG. 9 illustrates a top view of three manual flow selectors and associated needle valve assemblies for controlling the flow rate of three gases.

FIG. 9 illustrates a top view 900 of three manual flow selectors 910, 920, and 930 and associated needle valve assemblies 950, 951, and 952 for controlling the flow rate of three gases. In the illustrated embodiments, the manual flow selectors 910, 920, and 930 are illustrated as rotatable knobs. In alternative embodiments, the manual flow selectors may be configured as any of a wide variety of mechanical control selectors configured to directly adjust the flow rate of a mechanically controlled flow control valve. For example, the manual flow selectors 910, 920, and 930 may be configured as rotatable knobs, ratcheting knobs, dials, sliders, rotary switches, and the like.

A knob guard 940 may prevent each of the manual flow selectors 910, 920, and 930 from being actuated when in a retracted state, restrain axial motion relative to the front panel, and protect the manual flow selectors 910, 920, and 930.

Figure 10:
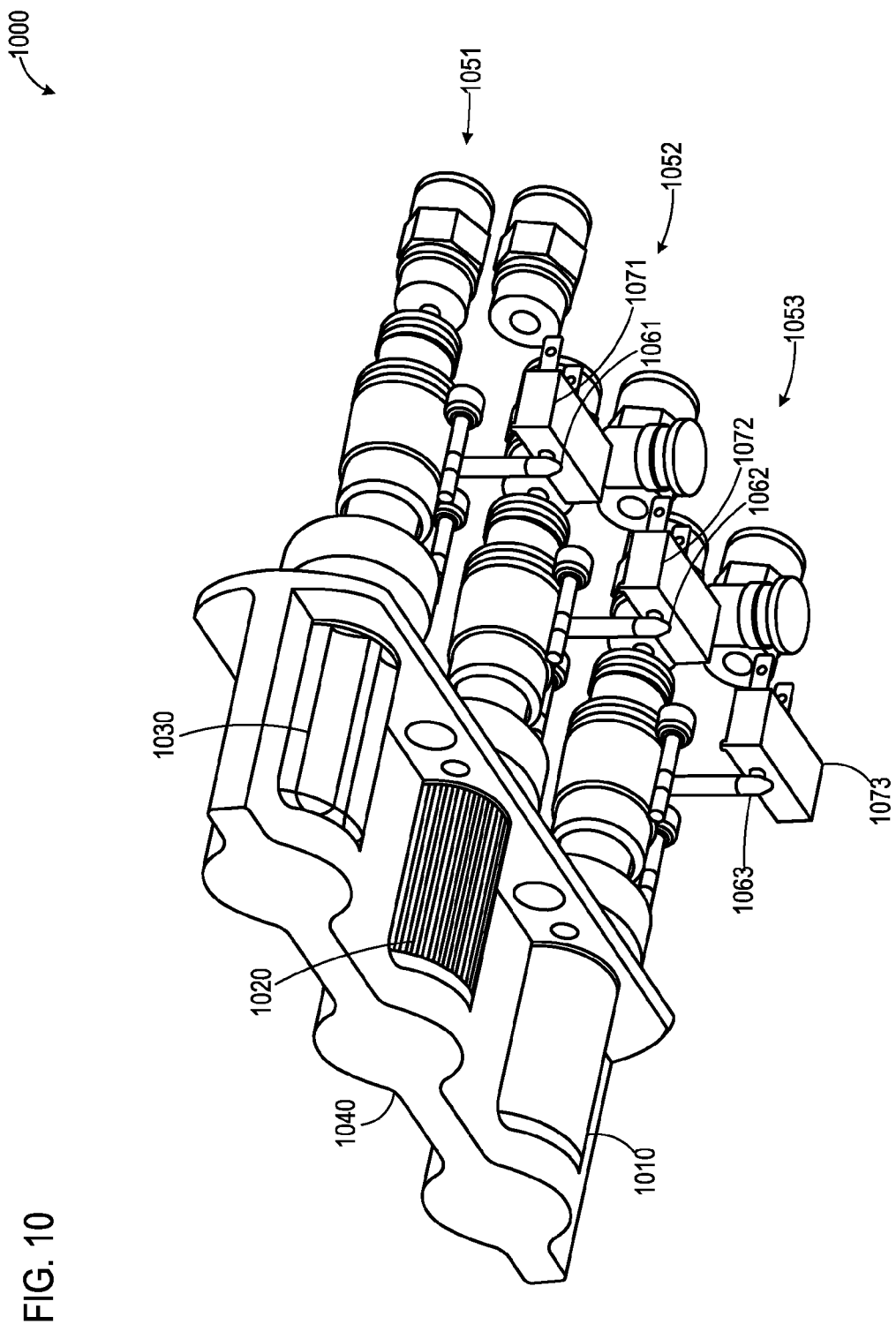
FIG. 10 illustrates a bottom view of three manual flow selectors and associated needle valve assemblies for controlling the flow rate of three gases.

FIG. 10 illustrates a bottom view 1000 of three manual flow selectors 1010, 1020, and 1030 and associated needle valve assemblies 1051, 1052, and 1053 for controlling the flow rate of three gases. Again, a knob guard 1040 may prevent each of the manual flow selectors 1010, 1020, and 1030 from being actuated when in a retracted state, prevent axial motion of the manual flow selectors 1010, 1020, and 1030 relative to the front panel, and protect the manual flow selectors 1010, 1020, and 1030. The knob guard 1040 may be configured to eliminate or reduce potential pinch points during the retraction and/or deployment of the manual flow selectors 1010, 1020, and 1030.

According to various embodiments, each manual flow selector 1010, 1020, and 1030 may have a non-circular recess that engages a corresponding non-circular tip of each respective needle valve 1051, 1052, and 1053 shaft configured to allow the needle valves 1051, 1052, and 1053 to move axially, independent of the manual flow selectors 1010, 1020, and 1030. Accordingly, the flow rate may be adjusted through axial displacement of each needle valve, yet remain rotationally connected to the knob in order to transmit the manual application of torque from a user.

As illustrated, each needle valve 1051, 1052, and 1053 may include a respective valve stop plunger 1061, 1062, and 1063 and position switch 1071, 1072, and 1073, which may function to detect when each respective needle valve 1051, 1052, and 1053 is fully closed or in a home state, as described herein.

Figure 11:
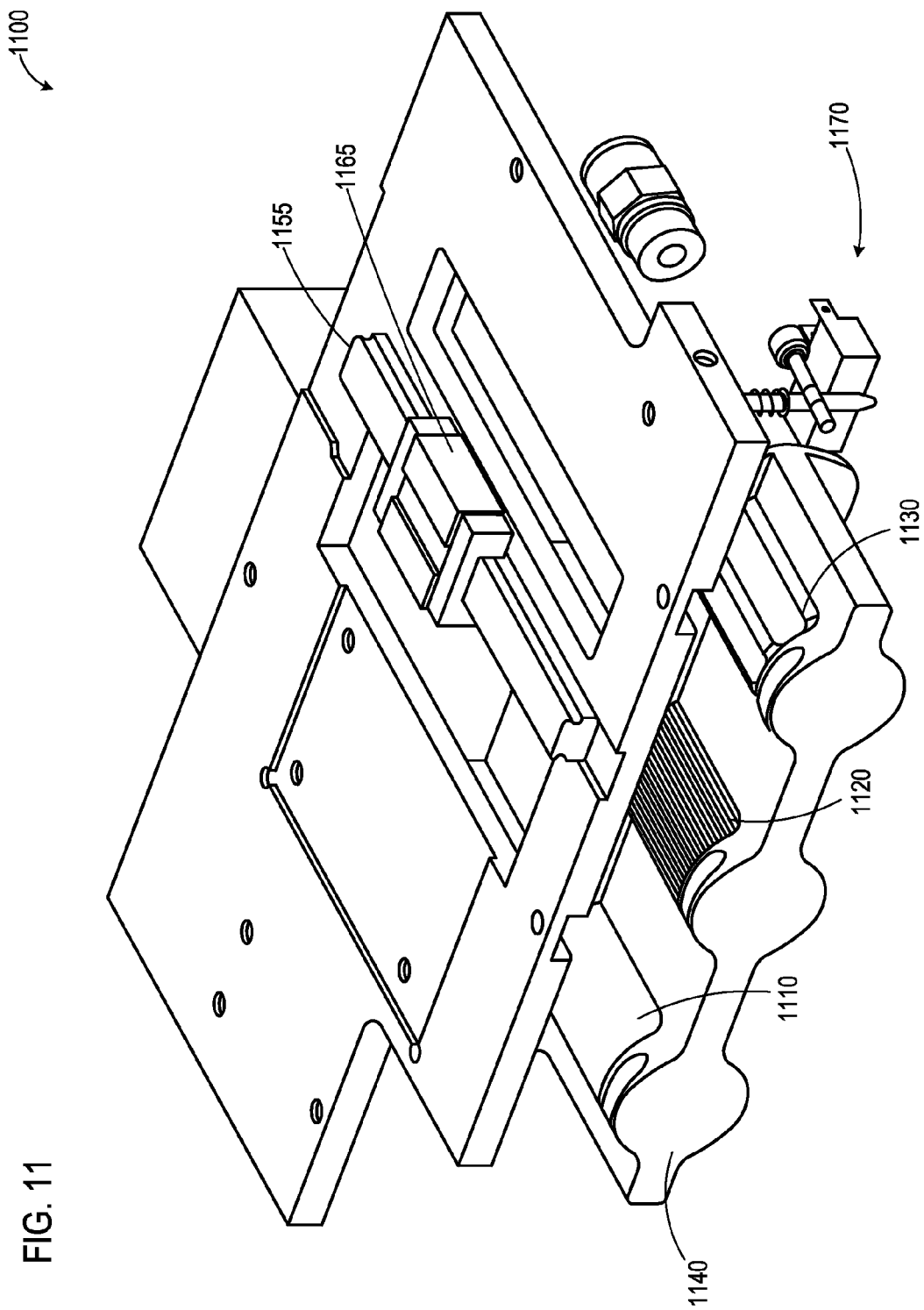
FIG. 11 illustrates carriage and rail assembly configured to slidably connect the flow selector assembly to a deployment assembly.

FIG. 11 illustrates an assembly 1100 including a carriage 1155 and rail 1165 configured to slidably connect the flow selector assembly 1170 to a deployment assembly (not shown). As illustrated, the flow selector assembly 1170 may include one or more (shown as three) manual flow selectors 1110, 1120, and 1130. A knob guard 1140 may prevent the manual flow selectors 1110, 1120, and 1130 from being actuated when in a retracted state, restrain axial motion relative to the front panel, and protect the manual flow selectors 1110, 1120, and 1130.

The carriage 1155 and rail 1165 assembly may be configured to slidably connect the flow selector assembly 1170 to a deployment assembly, such that the deployment assembly may slidably deploy the flow selector assembly by translating the carriage 1155 along the rail 1165. In alternative embodiments, the carriage 1155 and rail 1165 assembly may be replaced using another mechanism adapted for translating one apparatus relative to another apparatus.

Figure 12:
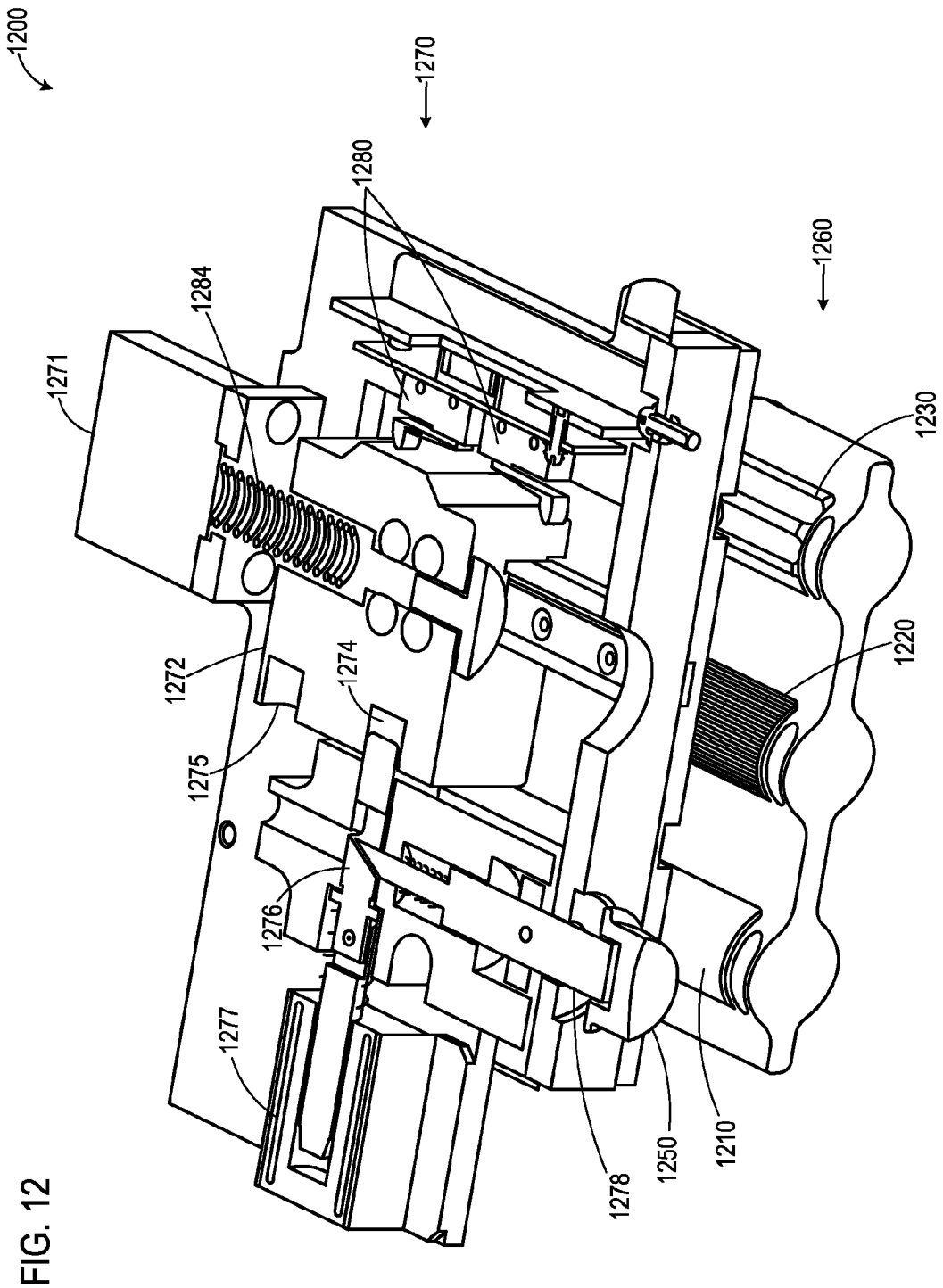
FIG. 12 illustrates a cut-away view of various components within a deployment assembly configured to selectively deploy manual flow selectors within a flow selector assembly.

FIG. 12 illustrates a mechanical apparatus 1200 cut-away view of various components within a deployment assembly 1270 configured to selectively deploy manual flow selectors 1210, 1220, and 1230 of a flow selector assembly 1260. As illustrated, the flow selector assembly 1260 may be latched in a retracted state by a solenoid latch pin 1276 secured within a first recess 1274 of a junction block 1272. Position switch(es) 1280 may detect the location of junction block 1272 in order to electronically or mechanically confirm the retracted state of the flow selector assembly 1260.

As illustrated, the flow selector assembly 1260 may be released and deployed by either an actuation of a manual override selector 1250 or by the actuation of solenoid 1277. If the manual override selector 1250 is actuated, an angled surface of a plunger 1278 may interact with the latch pin 1276, causing it to slide out of the first recess 1274 of the junction block 1272. If the manual override selector 1250 is pushed in sufficiently far and with sufficient force, the latch pin 1276 may disengage from the first recess 1274.

Alternatively, in response to a power failure, electronic failure, mechanical failure, software error, an electronic override selection, and/or other disruptive event, the solenoid 1277 and the latch pin 1276 may be pulled out of the first recess 1274, causing the system to enter a manual mode. In such situations, the junction block 1272 may be released from the locking effects of the latch pin 1276 and translate forward due to the force exerted by a deployment spring 1284. That is, the deployment spring 1284 may cause the junction block to translate forward. The flow selector assembly 1260, secured to the junction block 1272 on the rail and carriage assembly (see FIG. 11), may transition from the retracted state to a deployed state in which the flow control selectors 1210, 1220, and 1230 extend outward. The latch pin 1276 may engage the second recess 1275 and thereby lock the junction block in the deployed state.

According to the illustrated embodiment, in order to return to the retracted state, the solenoid 1277 may pull the latch pin 1276 from the second recess 1275 and the motor 1271 may pull the junction block back to a retracted state with the deployment spring 1284 in a compressed position. The latch pin 1276 may then lock the junction block in the retracted state by engaging the first recess 1274.

Figure 13:
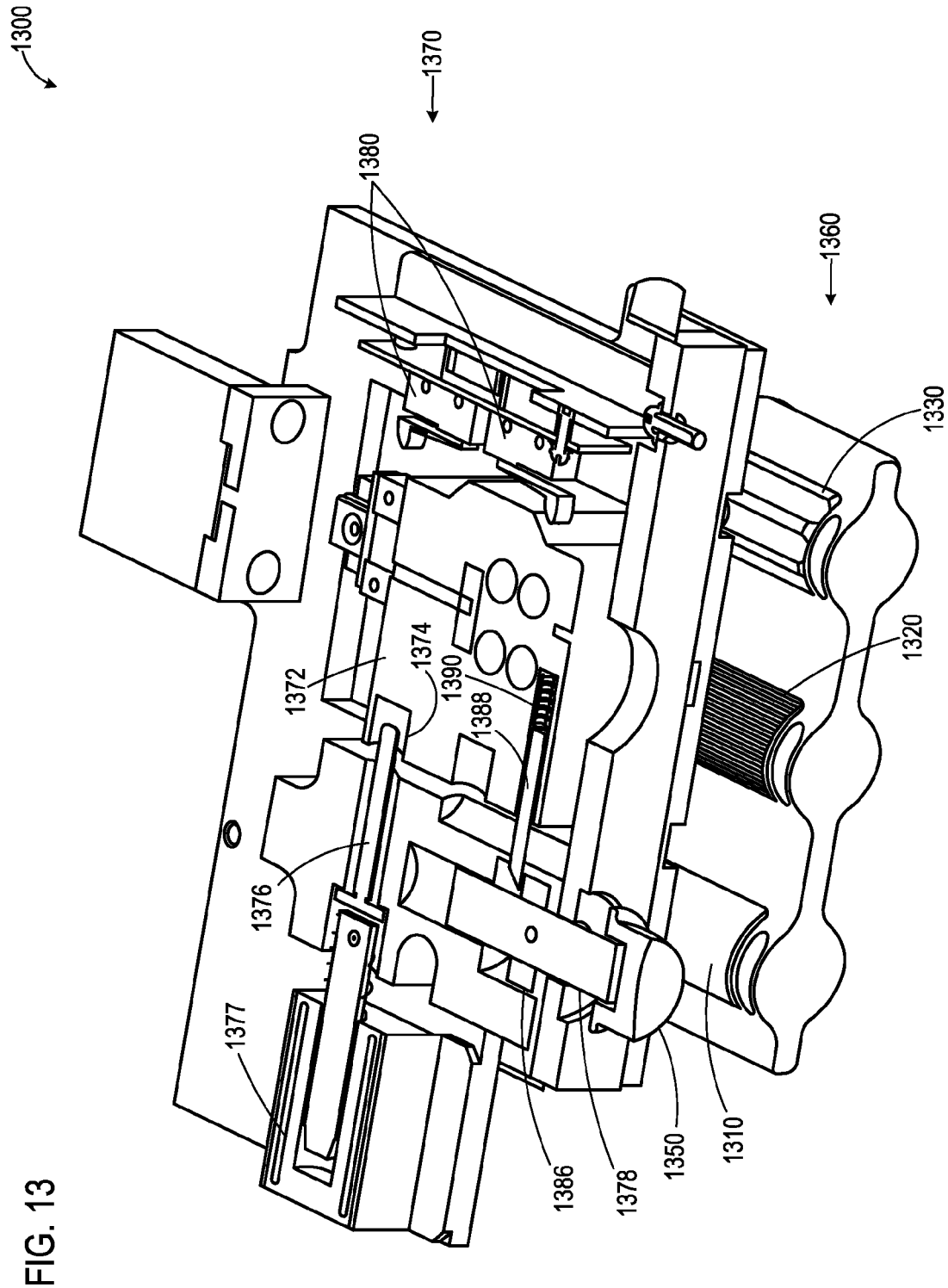
FIG. 13 illustrates a cut-away view of a deployment assembly with a flow selector assembly in a deployed state.

FIG. 13 illustrates the mechanical apparatus 1300, including a cut-away view of a deployment assembly 1370 with a flow selector assembly 1360 in a deployed state. As illustrated, the latch pin 1376 may engage the second recess 1374 to maintain the flow selector assembly in a deployed state until the solenoid 1377 is actuated. A spring loaded 1390 cross pin 1388 may engage a collar 1386 to prevent the plunger 1378 from being actuated via the plunger interface 1350.

Again, the position switch(es) 1380 may electronically and/or mechanically confirm that the junction block 1372 (and accordingly the flow selector assembly) is in a forward and deployed state. Flow control selectors 1310, 1320, and 1330 may then be used to manually adjust the flow rate of one or more gases by actuating and adjusting mechanically operated flow control valves, such as needle valves.

Figure 14:
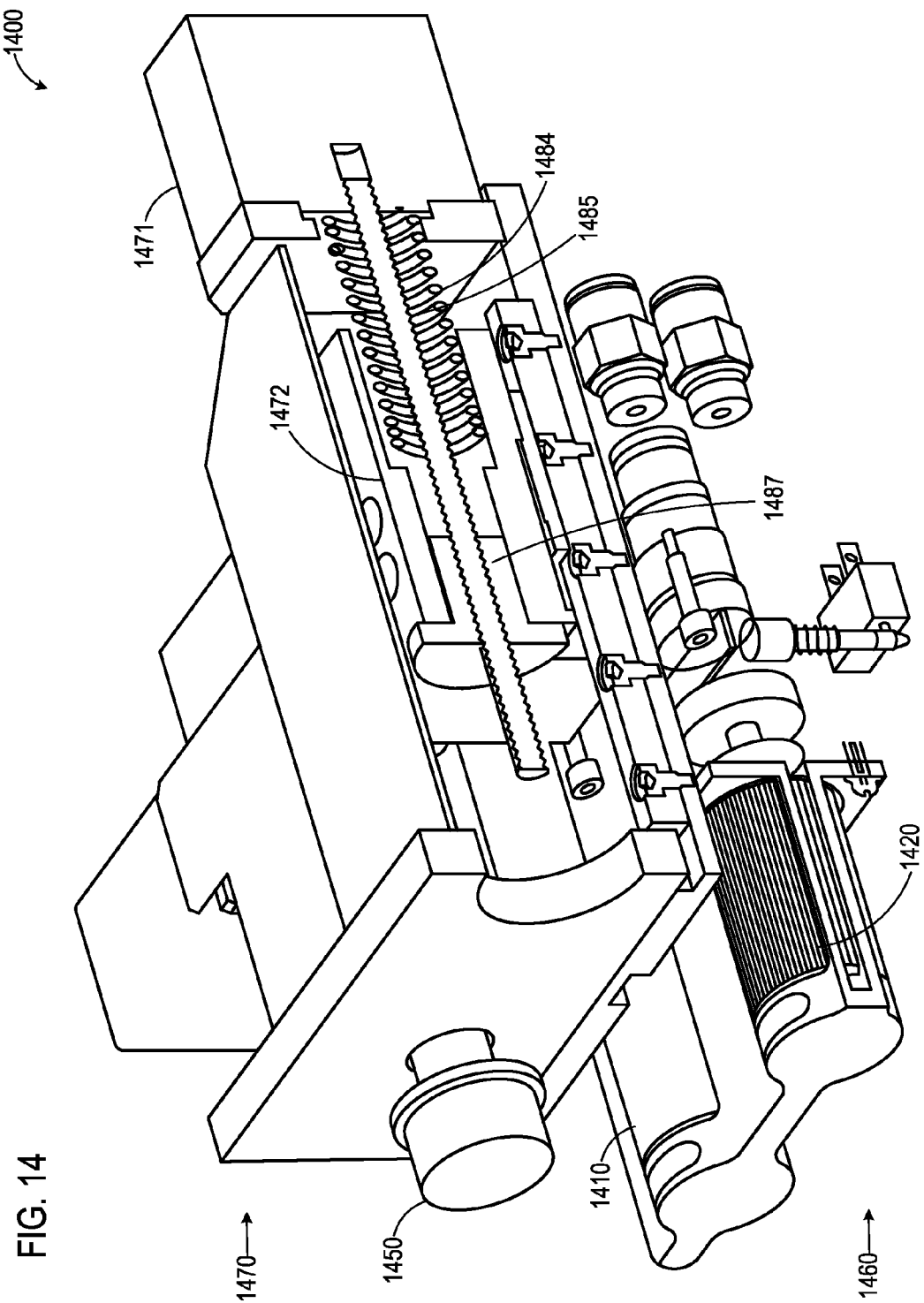
FIG. 14 illustrates a cut-away view of a portion of the deployment assembly.

FIG. 14 illustrates a cut-away view 1400 of a portion of the deployment assembly 1470 and the flow control assembly 1460. As illustrated, a motor 1471 may apply a torque to a threaded shaft 1485 to apply a translating force, via a threaded bushing 1487, to the junction block 1472. The force may be sufficient to overcome the deploying force of the deployment spring 1484. The button 1450 and associated plunger may be effectively reset for subsequent actuation. Manual flow control selectors 1410 and 1420 may be retracted in conjunction with the retraction of the junction block 1472.

Figure 15:
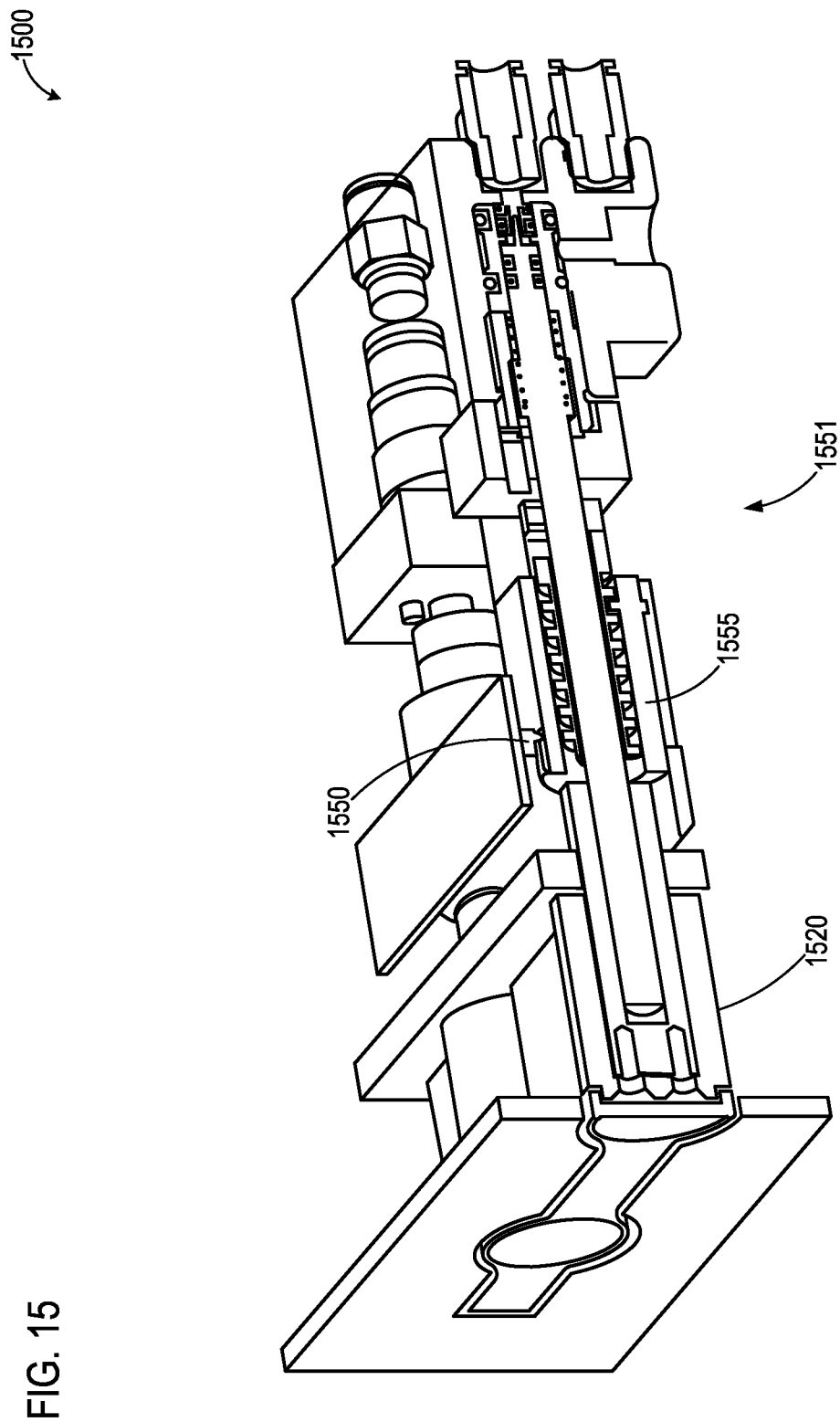
FIG. 15 illustrates a cut away view of a flow selector assembly in which detect switches confirm that the mechanical needle valves are in a home state.

FIG. 15 illustrates a cut away view of a flow selector assembly 1500 in which a detect switch 1550 confirms that a mechanical needle valve 1551 is in a home state by detecting a location with an axially-floating bushing 1555. According to various embodiments, the mechanical needle valve 1551 may be adjustable between a fully closed state, in which no gas flows, a fully open state, in which a maximum amount of gas flows, and any flow rate therebetween. In some embodiments, a needle valve may be configured to enter a home state when the flow control selector 1520 is retracted. The home state may correspond to a predetermined default flow rate.

A three-way selector valve (or other diversion valve system) may prevent any actual gas from flowing when the flow control selector 1520 is retracted. Accordingly, when the flow control selector 1520 is deployed, it may automatically allow an amount of gas corresponding to the home state of the mechanical needle valve 1551 to flow. For example, the home state may correspond to a flow rate of oxygen of 2 liters per minute and a flow rate of nitrous oxide and/or air of 0 liters per minute. Various possible home state flow rates are possible for each available gas.

Figure 16:
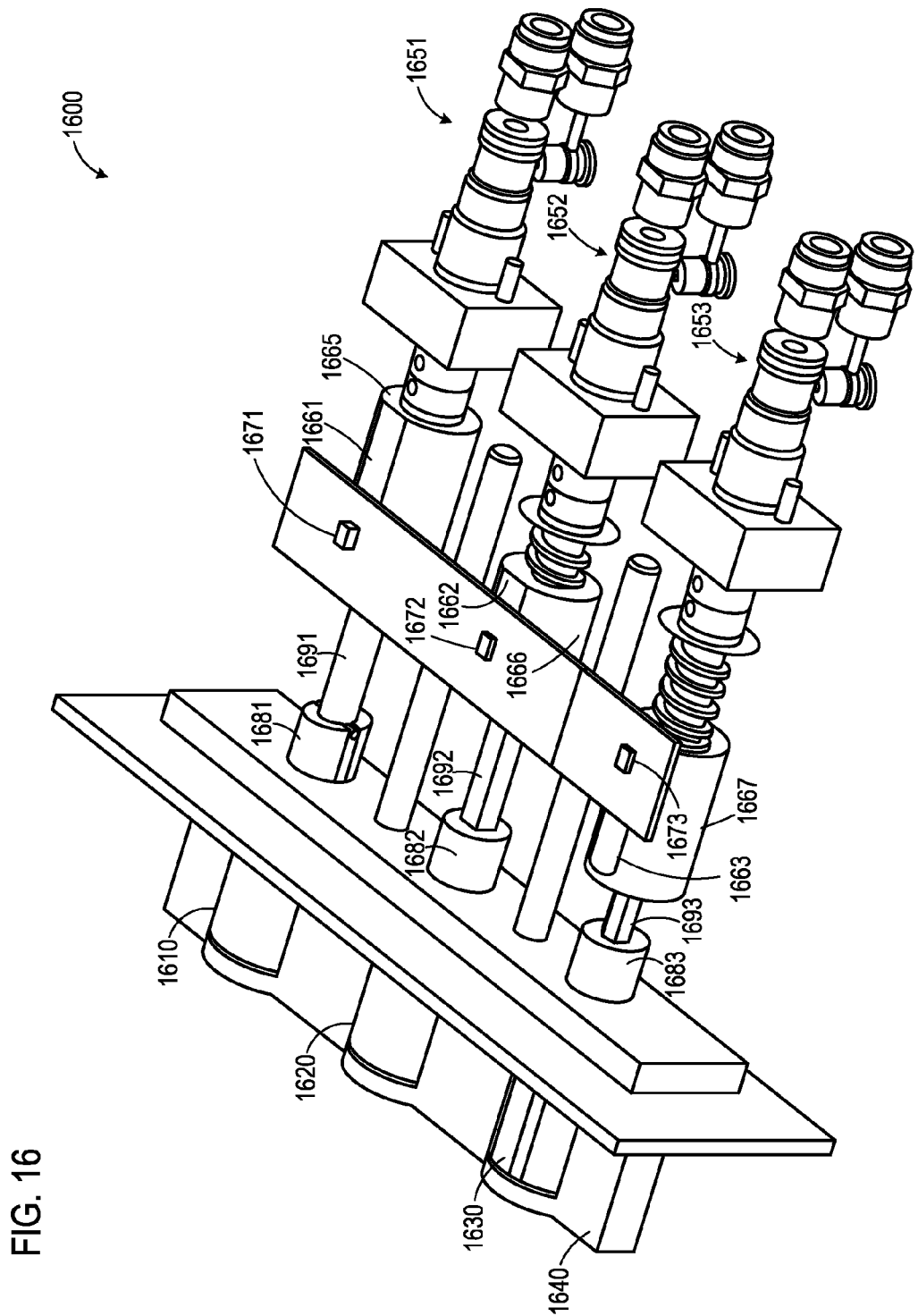
FIG. 16 illustrates a view of a flow selector assembly with position detectors configured to selectively detect the relative location of valve shafts and associated flow rates.

FIG. 16 illustrates another view of a flow selector assembly 1600 with position detectors (detect switches 1671, 1672, and 1673) configured to selectively detect the relative location of valve shafts 1691, 1692, and 1693. The position detectors 1671, 1672, and 1673 may be configured to detect whether or not they are engaged with protrusions (such as protrusion 1663) on a groove 1661, 1662, and 1663 on a bushing 1665, 1666, and 1667.

In the illustrated embodiment, needle valves 1651 and 1652 may be fully closed with the valve shafts 1691 and 1692 fully translated toward the needle valves 1651 and 1652. Accordingly, position detectors 1671 and 1672 may engage a protrusion (not illustrated) and detect that the needle valves 1651 and 1652 are fully closed. Valve shaft 1693 may be fully translated toward the flow selector 1630, causing needle valve 1653 to be fully opened. Position detector 1673 may not be engaged with protrusion 1663, and therefore detect that the needle valve 1653 is not fully closed.

FIG. 16 also shows three possible embodiments of valve shaft shapes. A first valve shaft 1693 may be hexagonal in shape and configured to engage a hexagonal cavity 1683 of a flow selector 1630. A second valve shaft 1692 may be rectangular in shape and configured to engage a rectangular cavity 1682 of a flow selector 1620. A third valve shaft 1691 may be circular in shape and include two protrusions configured to engage corresponding inclusions in a round cavity of a flow selector 1610. According to various embodiments, the cavities 1681, 1682, and 1683 may rotationally engage the valve shafts 1691, 1692, and 1693, but leave the valve shafts 1691, 1692, and 1693 free to axially translate relative to the flow selectors 1610, 1620, and 1630. In various embodiments, a knob guard 1640 may prevent axial translation of the flow selectors 1610, 1620, and 1630.

In some embodiments, locking mechanisms (not shown) may be utilized to selectively prevent the needle valves 1651, 1652, and 1653 from being actuated. The locking mechanisms may be automatically disengaged when the flow selectors 1610, 1620, and 1630 are deployed. Alternatively, the locking mechanisms may be independently engaged and disengaged by a user.

Figure 17:
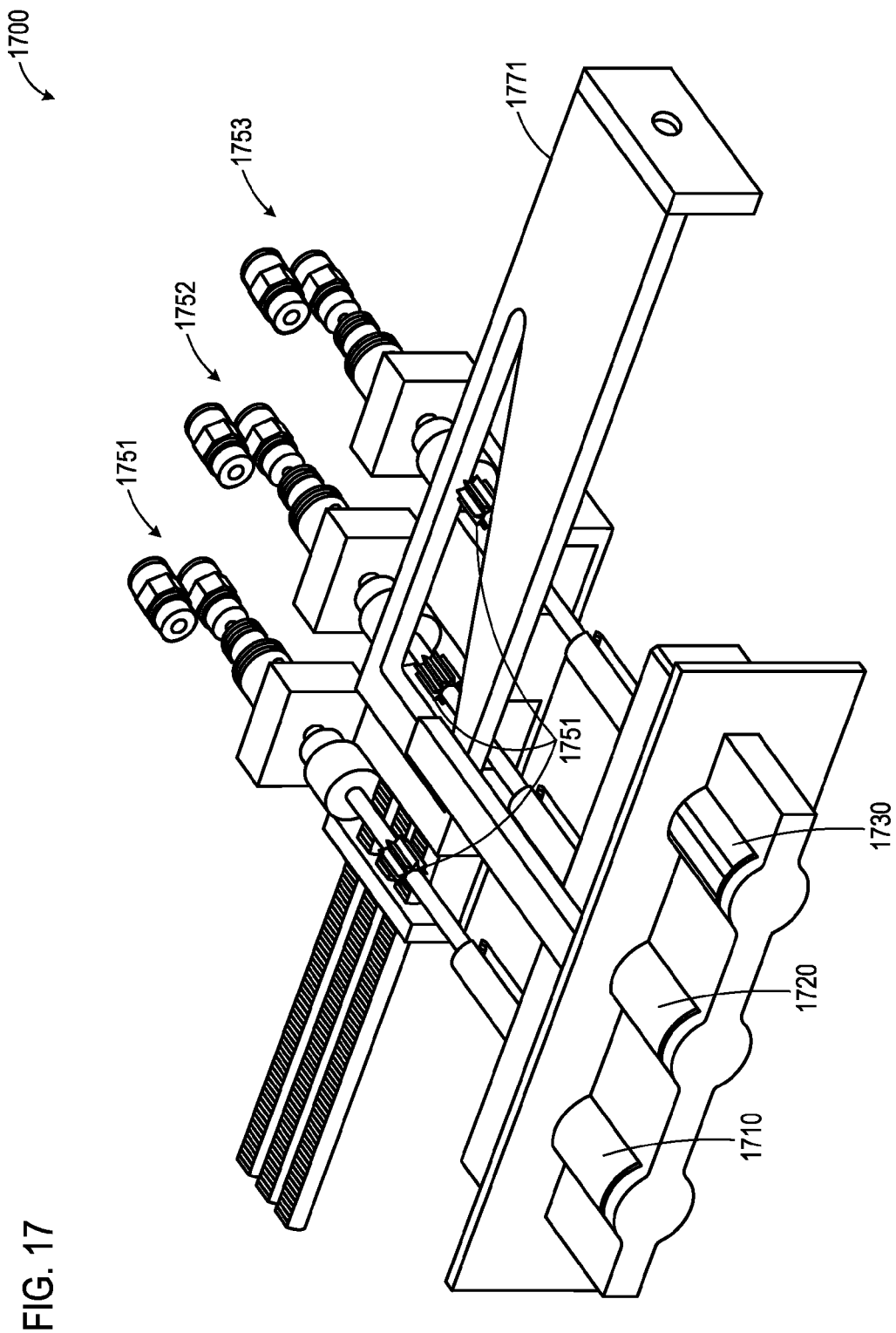
FIG. 17 illustrates an embodiment of a flow selector assembly configured with a home state assembly configured to return the needle valves to a home state when the deployment assembly retracts the flow selector assembly.

FIG. 17 illustrates an embodiment of a flow selector assembly 1700 configured with a home state assembly 1771 configured to return the needle valves to a home state when the deployment assembly retracts the flow selector assembly. According to various embodiments, the needle valves may be adjustable between a fully closed state, in which no gas flows, a fully open state, in which a maximum amount of gas flows, and any flow rate therebetween. In some embodiments, one or more of the needle valves may be configured to enter a home state when the flow control selectors 1710, 1720, and 1730 are retracted. The home state may correspond to a predetermined default flow rate of one or more gases. As illustrated, upon retraction of the flow control assembly 1700, a home state assembly 1771 may slidably engage gears 1751, to cause the needle valves to return to a default flow rate.

As previously described, a three-way selector valve (or other diversion valve system) may prevent any actual gas from flowing when a flow control selector is retracted. In such an embodiment, when the flow control selector assembly is deployed, it will automatically allow an amount of gas corresponding to the home state of the needle valve to flow. For example, the home state may correspond to a flow rate of oxygen of 2 liters per minute and a flow rate of nitrous oxide and/or air of 0 liters per minute. Various possible home state flow rates are possible for each available gas.

A gas flow control system, according to any of the various embodiments described herein, may be used in conjunction with any of a wide variety of applications. In the illustrated embodiments, the gas flow control systems are shown as parts of anesthesia delivery systems. In such embodiments, the combined flow of one or more gases may be injected or otherwise infused with anesthesia, such as via a vaporizer, for a controlled delivery of the anesthesia and/or the one or more gases to a patient.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. A fluid flow control system, comprising:
   an electronic flow control valve configured to selectively receive a first fluid from a first fluid supply;
   an electronic flow selector configured to allow for a selection of a flow rate of the first fluid from the first fluid supply via the electronic flow control valve;
   a controller configured to transmit a control signal to the electronic flow control valve to cause the electronic flow control valve to allow the first fluid to flow at the flow rate selected via the electronic flow selector;
   a mechanical flow control valve configured to selectively receive the first fluid from the first fluid supply;
   a manual flow selector configured to control a flow rate of the first fluid from the first fluid supply via the mechanical flow control valve; and
   an activation mechanism configured to:
      inhibit the operation of the manual flow selector when the fluid flow control system is in an electronic mode; and
      enable the operation of the manual flow selector when the fluid flow control system is in a manual mode.

2. The fluid flow control system of claim 1, wherein the activation mechanism comprises a deployment mechanism configured to:
   deploy the manual flow selector when the fluid flow control system is in the manual mode; and
   retract the manual flow selector when the fluid flow control system is in the electronic mode.

3. The fluid flow control system of claim 1, wherein the activation mechanism comprises a locking mechanism configured to:
   lock the manual flow selector to prevent adjustments when the fluid flow control system is in the electronic mode; and
   unlock the manual flow selector to allow adjustments when the fluid flow control system is in the manual mode.

4. The fluid flow control system of claim 1, further comprising a diversion valve system configured to:
   prevent the flow of the first fluid through the mechanical flow control valve and allow the flow of the first fluid through the electronic flow control valve when the fluid flow control system is in the electronic mode; and
   allow the flow of the first fluid through the mechanical flow control valve and prevent the flow of the first fluid through the electronic flow control valve when the fluid flow control system is in the manual mode.

5. The fluid flow control system of claim 4, wherein the diversion valve system comprises a three-way selector valve.

6. The fluid flow control system of claim 4, wherein the diversion valve system comprises:
   a normally-open valve configured to allow the flow of the first fluid through the mechanical flow control valve when the fluid flow control system is in the manual mode; and
   a normally-closed valve configured to prevent the flow of the first fluid through the electronic flow control valve when the fluid flow control system is in the manual mode.

7. The fluid flow control system of claim 1, further comprising a vaporizer configured to inject an anesthetic into the first fluid, and wherein the first fluid comprises a gas.

8. The fluid flow control system of claim 1, wherein the electronic flow control valve comprises an electronic proportional valve.

9. The fluid flow control system of claim 1, wherein the mechanical flow control valve comprises a needle valve.

10. The fluid flow control system of claim 1, wherein the mechanical flow control valve comprises a needle valve and the electronic flow control valve comprises a stepper motor configured to electronically control the needle valve.

11. The fluid flow control system of claim 1, wherein the manual flow selector comprises a rotatable knob.

12. The fluid flow control system of claim 1, wherein the controller comprises a hardware controller.

13. The fluid flow control system of claim 1, wherein the controller comprises a field-programmable gate array.

14. The fluid flow control system of claim 1, wherein the first fluid comprises one or more of oxygen, nitrous oxide, and air.

15. The fluid flow control system of claim 1, further comprising a manual override selector configured to cause the fluid flow control system to enter the manual mode when selected.

16. A method for providing a backup manual control for the flow of fluid in a flow control system, comprising:
   detecting that a flow control system is in an electronic mode;
   receiving a selection of a flow rate of a fluid via an electronic flow control selector;
   encoding the received selection of a flow rate as an electronic signal using an encoder;
   transmitting a control signal via a controller to an electronic flow control valve based on the encoded selection of a flow rate to cause the electronic flow control valve to allow the fluid to flow at the selected flow rate;

inhibiting the flow of the fluid through a mechanical flow control valve;

inhibiting the operation of a manual flow selector associated with the mechanical flow control valve; and receiving an instruction to enter a manual mode, and then:
 inhibiting the flow of the fluid through the electronic flow control valve;
 enabling the operation of the manual flow selector; and
 mechanically adjusting the flow rate of the fluid via the mechanical flow control valve in response to an adjustment of the manual flow selector.

17. The method of claim 16, wherein inhibiting the operation of the manual flow selector comprises retracting the manual flow selector when the flow control system is in the electronic mode, and
 wherein enabling the operation of the manual flow selector comprises deploying the manual flow selector when the flow control system is in the manual mode.

18. The method of claim 16, wherein inhibiting the operation of the manual flow selector comprises locking the manual flow selector when the flow control system is in the electronic mode to prevent adjustments, and
 wherein enabling the operation of the manual flow selector comprises unlocking the manual flow selector when the flow control system is in the manual mode to allow adjustments.

19. The method of claim 16, wherein inhibiting the flow of the fluid through the electronic flow control valve when the flow control system is in the manual mode and inhibiting the flow of the fluid through a mechanical flow control valve flow control system is in an electronic mode is performed using a diversion valve system comprising at least one of a three-way selector valve, a normally-open valve, and a normally-closed valve.

20. The method of claim 16, wherein the fluid comprises a gas and further comprising vaporizing an anesthetic into the gas.

21. The method of claim 16, wherein the electronic flow control valve comprises an electronic proportional valve.

22. The method of claim 16, wherein the mechanical flow control valve comprises a needle valve.

23. The method of claim 16, wherein the mechanical flow control valve comprises a needle valve and the electronic flow control valve comprises a stepper motor configured to electronically control the needle valve.

24. The method of claim 16, wherein the manual flow selector comprises a rotatable knob.

25. The method of claim 16, wherein the fluid comprises one or more of oxygen, nitrous oxide, and air.

26. The method of claim 16, wherein receiving an instruction to enter a manual mode comprises receiving an instruction from a manual override selector configured to cause the flow control system to enter the manual mode.

27. The method of claim 16, wherein receiving an instruction to enter a manual mode comprises detecting that the flow control system is in an unpowered state.

28. The method of claim 16, wherein receiving an instruction to enter a manual mode comprises detecting an error in the electronic mode.

* * * * *